(12) United States Patent
Sherman et al.

(10) Patent No.: US 11,660,209 B2
(45) Date of Patent: May 30, 2023

(54) ACETABULAR CUP PROSTHESIS ALIGNMENT SYSTEM AND METHOD

(71) Applicant: DePuy Synthes Products, Inc., Raynham, MA (US)

(72) Inventors: Jason T. Sherman, Warsaw, IN (US); Alec A. Birkbeck, Leeds (GB); Robert R. Freeman, Leeds (GB)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 160 days.

(21) Appl. No.: 17/242,981

(22) Filed: Apr. 28, 2021

(65) Prior Publication Data

US 2021/0244549 A1 Aug. 12, 2021

Related U.S. Application Data

(60) Continuation of application No. 16/354,944, filed on Mar. 15, 2019, now Pat. No. 11,026,811, which is a
(Continued)

(51) Int. Cl.
*A61F 2/46* (2006.01)
*A61B 34/20* (2016.01)
(Continued)

(52) U.S. Cl.
CPC ............ *A61F 2/4609* (2013.01); *A61B 34/20* (2016.02); *A61B 34/25* (2016.02); *A61F 2/4657* (2013.01);
(Continued)

(58) Field of Classification Search
CPC ...................... A61B 2034/2048; A61F 2/4609
See application file for complete search history.

(56) References Cited

U.S. PATENT DOCUMENTS

| 897,468 A | 9/1908 | Laflin |
|---|---|---|
| 3,001,975 A | 9/1961 | Beavers et al. |

(Continued)

FOREIGN PATENT DOCUMENTS

| WO | 2004091419 A2 | 10/2004 |
|---|---|---|
| WO | 2004112610 A2 | 12/2004 |

(Continued)

OTHER PUBLICATIONS

Indian Examination Report for Indian Application No. 8422/DELNP/2015, dated Oct. 13, 2020, 8 pages.
(Continued)

*Primary Examiner* — Matthew J Lawson
(74) *Attorney, Agent, or Firm* — Barnes & Thornburg LLP

(57) ABSTRACT

Technologies for aligning an acetabular prosthetic component in a patient's surgically prepared acetabulum include a reference sensor module securable to the patient's bony anatomy, an inserter sensor module securable to an acetabular prosthetic component inserter, and a display module. Each sensor module generates sensor data indicative of the orientation of the sensor module and/or structures to which the sensor module is coupled. The display module receives the sensor data from the sensor modules, determines the orientation of the acetabular prosthetic component relative to the patient's bony anatomy, and displays indicia of the determined orientation on a display.

12 Claims, 20 Drawing Sheets

Related U.S. Application Data continuation of application No. 15/451,604, filed on Mar. 7, 2017, now Pat. No. 10,265,193, which is a division of application No. 13/834,993, filed on Mar. 15, 2013, now Pat. No. 9,585,768.

(51) Int. Cl.
*A61B 34/00* (2016.01)
*A61F 2/34* (2006.01)

(52) U.S. Cl.
CPC ......... *A61B 2034/2048* (2016.02); *A61F 2/34* (2013.01); *A61F 2002/4629* (2013.01); *A61F 2002/4632* (2013.01); *A61F 2002/4668* (2013.01)

(56) References Cited

U.S. PATENT DOCUMENTS

| | | | |
|---|---|---|---|
| 6,205,411 B1 | 3/2001 | DiGioia et al. | |
| 6,656,117 B2 | 12/2003 | Jentsch et al. | |
| 6,991,655 B2 | 1/2006 | Iversen | |
| 7,825,815 B2 | 11/2010 | Shears et al. | |
| 7,877,131 B2 | 1/2011 | Jansen et al. | |
| 8,241,296 B2 | 8/2012 | Wasielewski | |
| 8,267,938 B2 * | 9/2012 | Murphy | B43L 7/10 |
| | | | 606/91 |
| 8,449,551 B2 | 5/2013 | Amiot et al. | |
| 8,588,892 B2 * | 11/2013 | Hladio | A61F 2/4609 |
| | | | 600/431 |
| 8,774,855 B2 | 7/2014 | Sanchez et al. | |
| 8,814,877 B2 | 8/2014 | Wasielewski | |
| 8,888,786 B2 | 11/2014 | Stone et al. | |
| 8,974,467 B2 | 3/2015 | Stone | |
| 8,994,826 B2 | 3/2015 | Bentley | |
| 8,998,910 B2 | 4/2015 | Borja et al. | |
| 9,115,998 B2 | 8/2015 | Proulx et al. | |
| 9,144,470 B2 | 9/2015 | Proulx et al. | |
| 9,192,392 B2 | 11/2015 | van der Walt et al. | |
| 9,198,659 B2 | 12/2015 | Beetel | |
| 9,265,447 B2 | 2/2016 | Stein et al. | |
| 9,271,756 B2 | 3/2016 | van der Walt et al. | |
| 10,265,193 B2 | 4/2019 | Sherman et al. | |
| 2002/0077540 A1 | 6/2002 | Kienzle, III | |
| 2004/0152970 A1 | 8/2004 | Hunter et al. | |
| 2004/0243148 A1 | 12/2004 | Wasielewski | |
| 2005/0149050 A1 | 7/2005 | Stifter et al. | |
| 2006/0094958 A1 | 5/2006 | Marquart et al. | |
| 2006/0095047 A1 | 5/2006 | de la Barrera | |
| 2006/0184177 A1 * | 8/2006 | Echeverri | A61B 17/1746 |
| | | | 606/91 |
| 2006/0189864 A1 | 8/2006 | Paradise et al. | |
| 2008/0255584 A1 | 10/2008 | Beverland et al. | |
| 2009/0099570 A1 | 4/2009 | Paradis et al. | |
| 2009/0171370 A1 * | 7/2009 | Yoon | A61F 2/4609 |
| | | | 606/130 |
| 2010/0100081 A1 | 4/2010 | Tuma et al. | |
| 2010/0249657 A1 | 9/2010 | Nycz et al. | |
| 2011/0092858 A1 | 4/2011 | Burger et al. | |
| 2012/0157887 A1 * | 6/2012 | Fanson | A61F 2/46 |
| | | | 600/595 |
| 2012/0209117 A1 | 8/2012 | Mozes et al. | |
| 2012/0245647 A1 | 9/2012 | Kunz et al. | |
| 2012/0316567 A1 | 12/2012 | Gross et al. | |
| 2013/0053859 A1 | 2/2013 | Penenberg | |
| 2013/0066323 A1 | 3/2013 | Nycz et al. | |
| 2013/0274633 A1 * | 10/2013 | Hladio | A61B 5/1072 |
| | | | 600/587 |
| 2014/0005531 A1 | 1/2014 | Taylor | |
| 2014/0031829 A1 * | 1/2014 | Paradis | A61B 34/20 |
| | | | 606/102 |
| 2014/0052149 A1 * | 2/2014 | van der Walt | A61F 2/4609 |
| | | | 606/130 |
| 2014/0094925 A1 * | 4/2014 | Satterthwaite | A61F 2/4684 |
| | | | 606/91 |
| 2014/0198766 A1 | 7/2014 | Siomina et al. | |
| 2014/0229196 A1 | 8/2014 | Perkins | |
| 2014/0276871 A1 | 9/2014 | Sherman et al. | |
| 2016/0029952 A1 | 2/2016 | Hunter | |

FOREIGN PATENT DOCUMENTS

| | | |
|---|---|---|
| WO | 2012024271 A2 | 2/2012 |
| WO | 2012171555 A1 | 12/2012 |
| WO | 2013059246 A1 | 4/2013 |

OTHER PUBLICATIONS

International Search Report and Written Opinion for International Application No. PCT/US2014/018889, dated May 26, 2014, 6 pages.

* cited by examiner

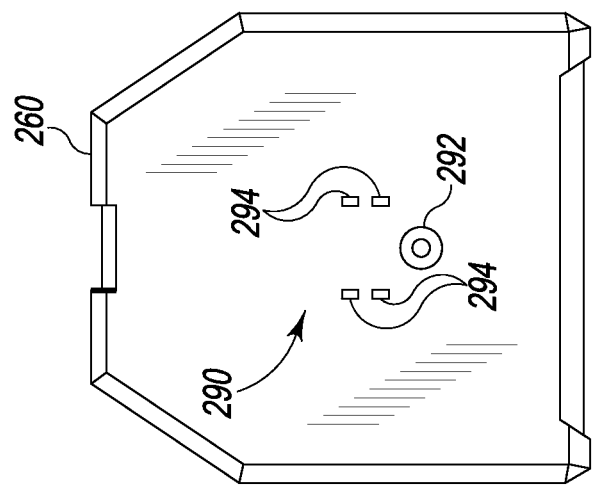
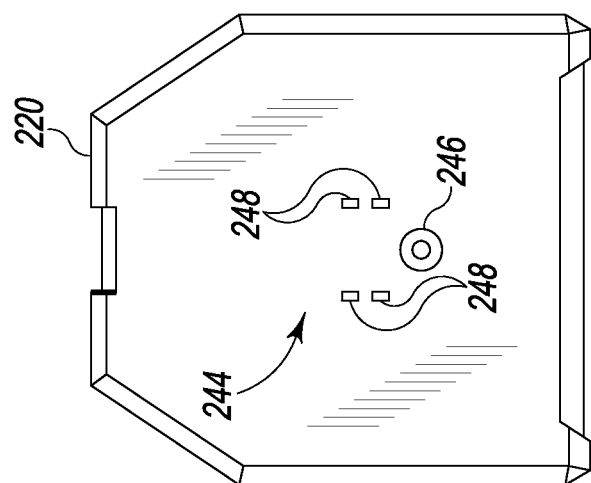
Fig. 4

$$R = \begin{bmatrix} 1-2*qy^2-2*qz^2 & 2*qx*qy-2*qz*qw & 2*qx*qz+2*qy*qw \\ 2*qx*qy+2*qz*qw & 1-2*qx^2-2*qz^2 & 2*qy*qz-2*qx*qw \\ 2*qx*qz-2*qy*qw & 2*qy*qz+2*qx*qw & 1-2*qx^2-2*qy^2 \end{bmatrix}$$

$$V_A = R_A * \begin{bmatrix} 1 \\ 0 \\ 0 \end{bmatrix}$$

2102

$$V_B = R_B * \begin{bmatrix} -1 \\ 0 \\ 0 \end{bmatrix}$$

2104

$$V_C = V_A \times V_B$$

$$V_B = V_C \times V_A$$

Fig. 22

$$R_p = \begin{bmatrix} V_B & \cdot & \cdot & \cdot \\ V_C & \cdot & \cdot & \cdot \\ V_A & \cdot & \cdot & \cdot \end{bmatrix} = \begin{bmatrix} r_{11} & \cdot & \cdot & r_{13} \\ \cdot & \cdot & \cdot & \cdot \\ \cdot & \cdot & \cdot & \cdot \\ r_{31} & \cdot & \cdot & r_{33} \end{bmatrix}$$

$$Q_p = \begin{bmatrix} q_w \\ q_x \\ q_y \\ q_z \end{bmatrix} = \begin{bmatrix} \sqrt{1 + r_{11} + r_{22} + r_{22}}/2 \\ (r_{32} - r_{23})/4 * q_w \\ (r_{13} - r_{31})/4 * q_w \\ (r_{21} - r_{12})/4 * q_w \end{bmatrix}$$

$Q_{final} = Q_2^{-1} * Q_p$

ACETABULAR CUP PROSTHESIS ALIGNMENT SYSTEM AND METHOD

This continuation application claims priority under 35 U.S.C. § 120 to U.S. patent application Ser. No. 16/354,944, which was filed on Mar. 15, 2019 and claims priority to U.S. patent application Ser. No. 15/451,604, now U.S. Pat. No. 10,265,193, which was filed on Mar. 7, 2017 and claims priority under 35 U.S.C. § 121 to U.S. patent application Ser. No. 13/834,993, now U.S. Pat. No. 9,585,768, which was filed on Mar. 15, 2013, each of which is expressly incorporated herein by reference.

TECHNICAL FIELD

The present disclosure relates generally to an implantable orthopaedic prosthesis, and more particularly to an implantable acetabular prosthesis and systems and methods of aligning acetabular prostheses during implantation.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments. The acetabular component is typically inserted into the patient's acetabulum using an acetabular prosthetic component inserter. Poor alignment of the acetabular prosthetic component relative to the patient's bony anatomy can result in component loosening and/or dislocation over time and use of the prosthetic hip joint.

SUMMARY

According to one aspect, a system for aligning an acetabular prosthetic component in a patient's surgically prepared acetabulum includes a reference sensor module securable to the patient's bony anatomy, an inserter sensor module securable to an acetabular prosthetic component inserter, and a display module separate from the reference sensor module and the inserter sensor module. The reference sensor module includes (i) a first orientation sensor configured to generate first sensor data indicative of the orientation of the patient's bony anatomy in three-dimensions and (ii) a first communication circuit to transmit the first sensor data. The inserter sensor module includes (i) a second orientation sensor configured to generate second sensor data indicative of the orientation of the acetabular prosthetic component inserter in three-dimensions, (ii) a second communication circuit to transmit the first sensor data, and (iii) an alignment indicator. The display module includes (i) a display, (ii) a third communication circuit configured to receive the first sensor data and the second sensor data, and (iii) a processing circuit to determine an orientation of an acetabular prosthetic component coupled to the acetabular prosthetic component inserter relative to the patient's bony anatomy based on the first sensor data and the second sensor data, display indicia of the determined orientation of the acetabular prosthetic component on the display, and communicate with the inserter sensor module to activate the alignment indicator in response to the determined orientation being within threshold amount of a reference orientation.

In some embodiments, the first orientation sensor may include a first three-axis gyroscope and a first three-axis accelerometer. Additionally or alternatively, the second orientation sensor may include a second three-axis gyroscope and a second three-axis accelerometer. In some embodiments, each of the reference sensor module and the inserter sensor module may include a power button selectable to turn on the corresponding sensor module. In such embodiments, each of the reference sensor module and the inserter sensor module may be incapable of being turned off by selection of the power button after the corresponding sensor module has been turned on.

In some embodiments, the alignment indicator may include a first alignment indicator and a second alignment indicator. In such embodiments, the processing circuit of the display module may be configured to (i) communicate with the inserter sensor module to activate the first alignment indicator in response to the determined orientation being within a first threshold amount of the reference orientation and (ii) communicate with the inserter sensor module to activate the second alignment indicator in response to the determined orientation being within a second threshold amount of the reference orientation that is less than the first threshold amount. Additionally, in some embodiments, the second alignment indicator may be bounded by the first alignment indicator.

Additionally, in some embodiments, the processing circuit of the display module may be configured to determine an inclination angle and an anteversion angle of the acetabular prosthetic component relative to the patient's bony anatomy and display the inclination angle and the anteversion angle on the display. Additionally or alternatively, the processing circuit of the display module may be configured to display a graphical representation of the acetabular prosthetic component inserter on the display in a position based on the determined inclination angle and anteversion angle.

In some embodiments, the processing circuit of the display module may be configured to determine a coordinate system conversion factor to convert the first sensor data from a coordinate system of the inserter sensor module to a patient coordinate system of the patient's bony anatomy and determine the orientation of the acetabular prosthetic component inserter relative to the patient's bony anatomy using the coordinate system conversion factor. Additionally, in some embodiments, the reference sensor module may include a housing having a first keyed structure and the inserter sensor module includes a housing having a second keyed structure. The first keyed structure and the second keyed structure may be keyed to each other such that the reference sensor module and the inserter sensor module can be coupled to each other in a single orientation in which the first keyed structure and the second keyed structure are mated. For example, in some embodiments, the first keyed structure may be embodied as a raised platform extending upwardly from a top surface of the housing of the reference sensor module and the second keyed structure may be embodied as a recess defined in a top surface of the housing of the inserter sensor module, wherein the raised platform is received in the recess when the reference sensor module and the inserter sensor module are coupled to each other in the single orientation.

Additionally, in some embodiments, the system may include an alignment frame. The alignment frame may include a frame body, a plurality of contact feet, and a cradle. In some embodiments, the contact feet may be movable relative to the frame body. Additionally or alternatively, the cradle may be sized to receive the inserter sensor module.

According to another aspect, a method for aligning an acetabular prosthetic component in a patient's surgically-prepared acetabulum includes securing a reference sensor module to the patient's bony anatomy, securing an inserter sensor module to an acetabular prosthetic component inserter, generating, with the reference sensor module, first sensor data indicative of the orientation of the patient's bony anatomy in three-dimensions, generating, with the inserter sensor module, second sensor data indicative of the orientation of the acetabular prosthetic component inserter in three-dimensions, receiving, with a display module, the first sensor data and the second sensor data, determining, with the display module, an orientation of an acetabular prosthetic component coupled to the acetabular prosthetic component inserter relative to the patient's bony anatomy based on the first sensor data and the second sensor data, displaying, on the display module, indicia of the determined orientation of the acetabular prosthetic component on a display of the display module, and transmitting a control signal from the display module to the inserter sensor module to activate an alignment indicator of the inserter sensor module in response to the determined orientation being within a threshold amount of a reference orientation.

In some embodiments, securing the reference sensor module to the patient's bony anatomy may include attaching the reference sensor module to a mounting frame and securing the mounting frame to the patient's bony anatomy. Additionally, in some embodiments, the method may also include initializing the reference sensor module and the inserter sensor module to compensate for bias offset of the corresponding generated sensor data. For example, initializing the reference sensor module and the inserter sensor module may include placing each of the reference sensor module and the inserter sensor module in a stationary position relative to each other. In some embodiments, placing each of the reference sensor module and the inserter sensor module in a stationary position relative to each other may include mating a keyed feature of a housing of the reference sensor module with a corresponding keyed feature of a housing of the inserter sensor module. Additionally or alternatively, initializing the reference sensor module and the inserter sensor module may include transmitting identification data from each the reference sensor module and the inserter sensor module to the display module and displaying the identification data on the display of the display module.

In some embodiments, the method may also include registering the inserter sensor module to a patient coordinate system of the patient's bony anatomy. For example, registering the inserter sensor module to the patient coordinate system may include aligning the inserter sensor module with a spine of the patient and aligning the inserter sensor module with an anatomical axis of the patient defined by the anterior superior iliac spine points of the patient's bony anatomy. In such embodiments, the method may also include generating, with the inserter sensor module, first alignment data indicative of the current orientation of the inserter sensor module while aligned with the spine of the patient, generating, with the inserter sensor module, second alignment data indicative of the current orientation of the inserter sensor module while aligned with the anatomical axis of the patient, and generating a coordinate system conversion factor based on the first and second alignment data to convert sensor data generated by the inserter sensor module from a coordinate system of the inserter sensor module to a patient coordinate system of the patient's bony anatomy. For example, determining the orientation of the acetabular prosthetic component may include determining the orientation of the acetabular prosthetic relative to the patient's bony anatomy based on the first sensor data and the coordinate system conversion factor.

In some embodiments, registering the inserter sensor module to the patient coordinate system may include placing an alignment frame on the patient in a position such that a first contact foot of the alignment frame confronts a first anterior superior iliac spine point of the patient, a second contact foot of the alignment frame confronts a second anterior superior iliac spine point of the patient, and a third contact foot of the alignment frame confronts a pubic symphysis of the patient. In such embodiments, the method may further include coupling the inserter module to the alignment frame.

Additionally, in some embodiments, determining the orientation of the acetabular prosthetic component may include determining an inclination angle and an anteversion angle of the acetabular prosthetic relative to the patient's bony anatomy. Additionally or alternatively, displaying indicia of the determined orientation of the acetabular prosthetic component may include displaying the inclination angle and the anteversion angle on the display of the display module. For example, displaying indicia of the determined orientation of the acetabular prosthetic component may include displaying a graphical representation of the acetabular prosthetic component inserter on the display in a position based on the determined inclination angle and anteversion angle.

According to a further aspect, a system for aligning an acetabular prosthetic component in a patient's surgically prepared acetabulum may include a reference sensor module securable to the patient's bony anatomy and an inserter sensor module securable to an acetabular prosthetic component inserter. The reference sensor module may include (i) a housing having a first keyed structure, a (ii) a first orientation sensor positioned in the housing and configured to generate first sensor data indicative of the orientation of the patient's bony anatomy in three-dimensions, and (iii) a first communication circuit to transmit the first sensor data. The inserter sensor module may include (i) a housing having a second keyed structure (ii) a second orientation sensor configured to generate second sensor data indicative of the orientation of the acetabular prosthetic component inserter in three-dimensions, (ii) a second communication circuit to transmit the first sensor data, and (iii) a housing having (iii) an alignment indicator. The first keyed structure and the second keyed structure may be keyed to each other such that the reference sensor module and the inserter sensor module can be coupled to each other in a single orientation in which the first keyed structure and the second keyed structure are mated.

In some embodiments, the first keyed structure may be embodied as a raised platform extending upwardly from a top surface of the housing of the reference sensor module. Additionally, the second keyed structure may be embodied as a recess defined in a top surface of the housing of the inserter sensor module, wherein the raised platform is received in the recess when the reference sensor module and the inserter sensor module are coupled to each other in the single orientation.

BRIEF DESCRIPTION OF THE DRAWINGS

The detailed description particularly refers to the following figures, in which:

FIG. 4 is a bottom plan view of the reference sensor module and the inserter sensor module of FIG. 2;

FIGS. 20-25 are illustration of various equations used to convert from the sensor coordinate system of FIG. 16 to the patient coordinate system of FIG. 17.

DETAILED DESCRIPTION OF THE DRAWINGS

Figure 1:
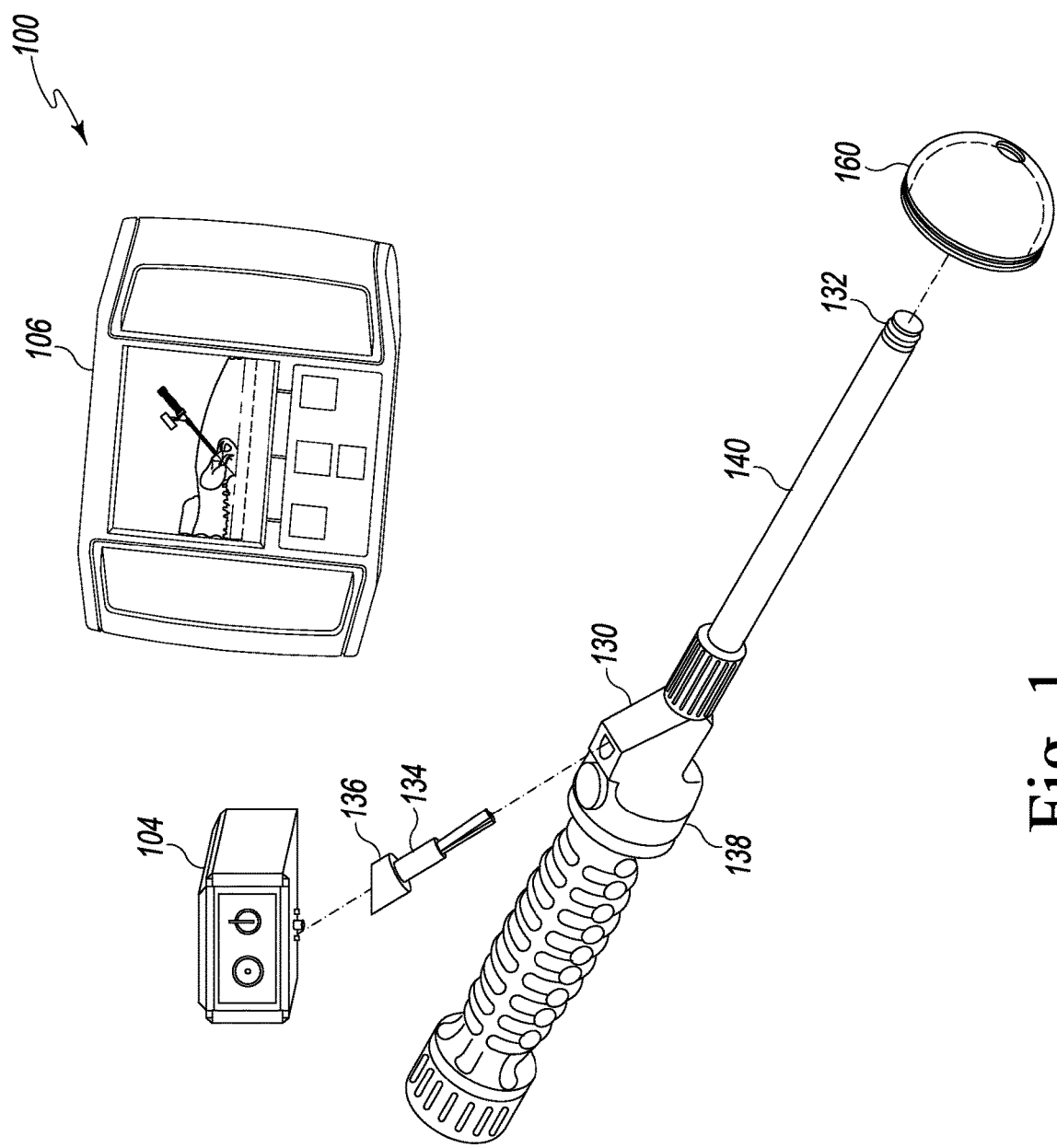
FIG. 1 is a simplified diagram of an system for aligning an acetabular prosthetic component in a patient's surgically prepared acetabulum.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, a system 100 for aligning an acetabular prosthetic component 160 in a patient's surgically prepared acetabulum includes a reference sensor module 102, an inserter sensor module 104, and a hand-held display module 106. In use, the reference sensor module 102 is secured to the bony anatomy of the patient using a mounting bracket 110 and generates sensor data indicative of the orientation of the reference sensor module 102, and thereby the patient's bony anatomy, in three dimensions (i.e., rotation about each coordinate axis x, y, and z). Similarly, the inserter sensor module 104 is attached to an acetabular prosthetic component inserter 130 and generates sensor data indicative of the orientation of the inserter sensor module 104, and thereby the acetabular prosthetic component inserter 130, in three dimensions. Each of the sensor modules 102, 104 transmit the generated sensor data to the display module 106. The display module 106 determines an orientation of the acetabular prosthetic component 160, which is secured to a distal end 132 of the acetabular prosthetic component inserter 130, relative to the patient's bony anatomy as discussed in more detail below.

Figure 2:
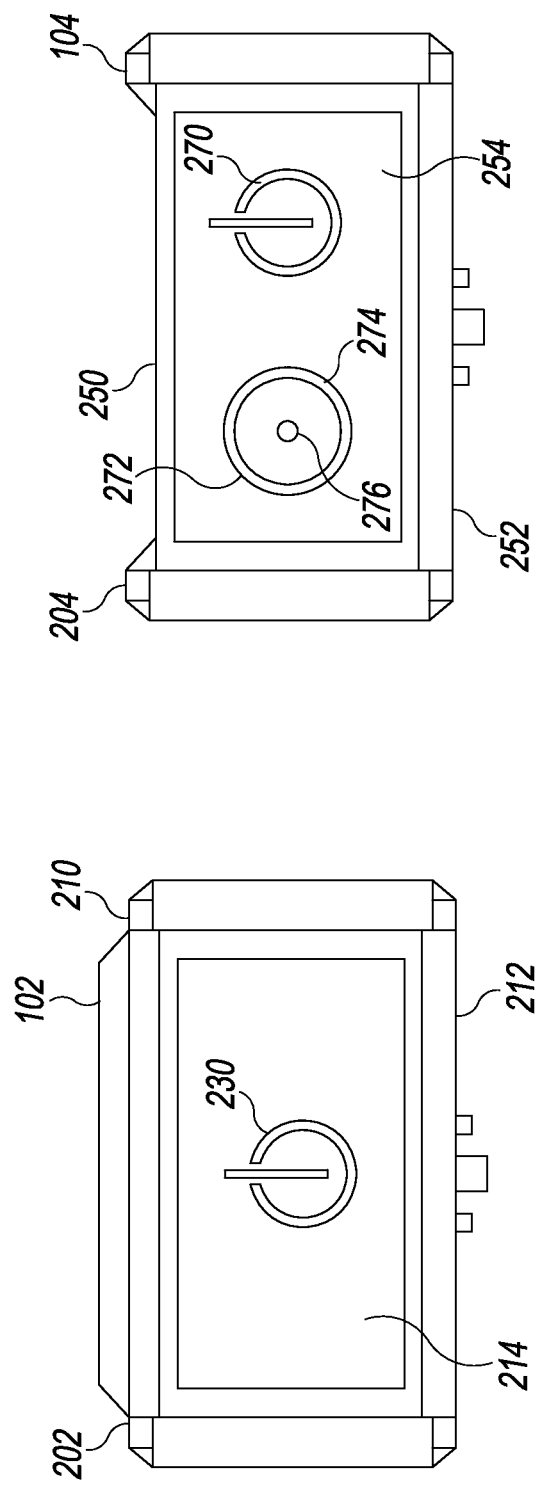
FIG. 2 is a front elevation view of a reference sensor module and an inserter sensor module of the system of FIG. 1.
Figure 3:
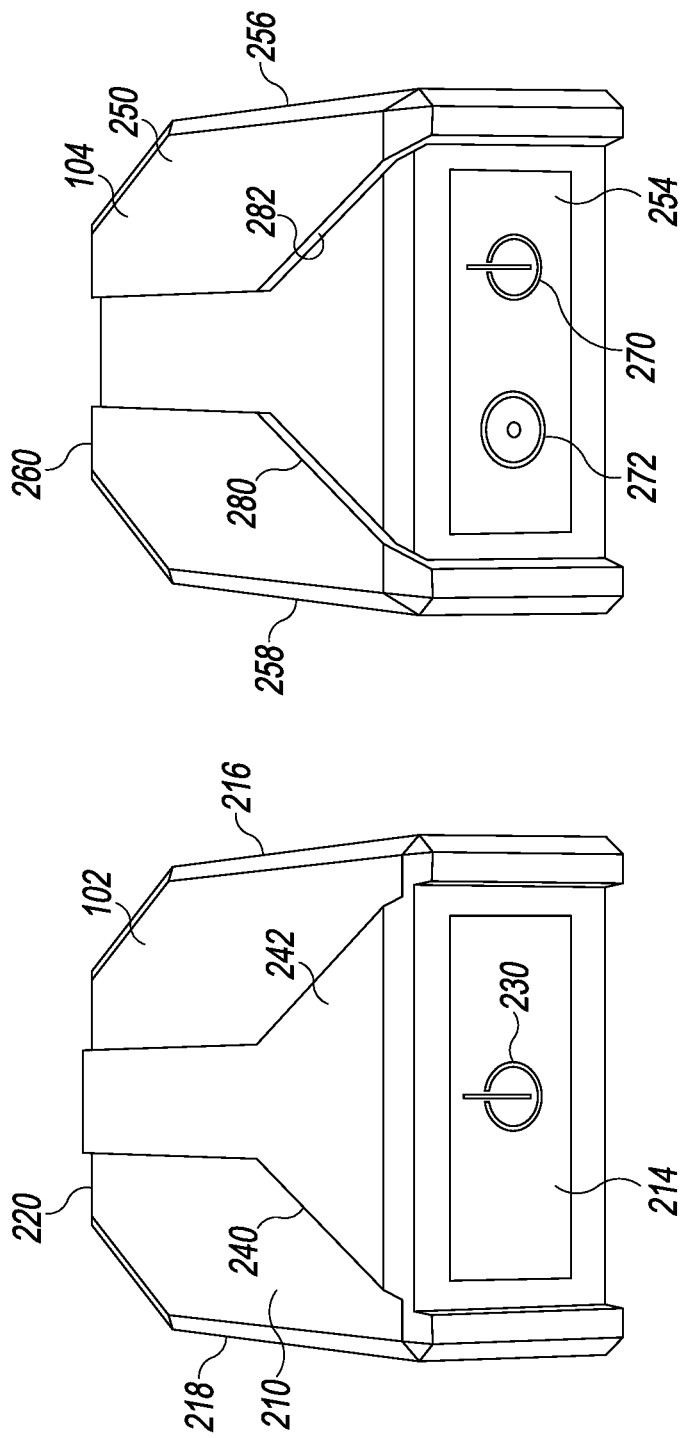
FIG. 3 is a top perspective view of the reference sensor module and the inserter sensor module of FIG. 2.

As shown in FIGS. 2-4, each of the sensor modules 102, 104 includes a corresponding housing 202, 204 having a generally rectangular shape. Illustratively, each housing 202, 204 is embodied as a multi-piece housing. However, housings having other shapes and configurations may be used in other embodiments.

The housing 202 of the reference sensor module 102 includes a top surface 210, a bottom surface 212, a front panel 214, side surfaces 216, 218, and a rear surface 220. The reference sensor module 102 also includes a power button 230 defined on the front panel 214. The power button 230 is selectable to turn on the reference sensor module 102. However, in some embodiments, the reference sensor module 102 may not be turned off after the sensor module 102 has been successfully turned on. That is, re-selection of the power button 230 does not turn off the reference sensor module 102. Rather, the reference sensor module 102 will remain on until the power source (e.g., internal batteries) of the reference sensor module 102 is depleted as discussed in more detail below. In some embodiments, the power button 230 is backlit when the reference sensor module 102 is turned on to provide a visual indication that the reference sensor module 102 is powered on.

As shown in FIG. 3, the housing 202 of the reference sensor module 102 also includes a keyed structure 240 defined on the top surface 210. In the illustrative embodiment, the keyed structure 240 is keyed to a corresponding keyed structure 280 of the inserter sensor module 104. As discussed in more detail below, the keyed structures 240, 280 facilitate the coupling together of the reference sensor module 102 and the inserter sensor module 104. Due to the keyed configuration of the keyed structures 240, 280, the sensor modules 102, 104 can be coupled together in only a single orientation relative to each other in which the keyed structures 240, 280 are mated together. In the illustrative embodiment, the keyed structure 240 is embodied as a raised platform 242 that extends upwardly from the top surface 210. The raised platform 242 has a substantially "Y"-shaped top profile and is arranged such that the width of the raised platform 242 is greater toward the front panel 214 and narrower toward the rear surface 220. Of course, in other embodiments, other configurations of the keyed structure 240 that enable coupling of the sensor modules 102, 104 in a single orientation in which the keyed structures 240, 280 are mated may be used. For example, in some embodiments, the keyed structure 240 may be embodied as, or otherwise include, a recess, additional raised platforms, and/or other structures.

The reference sensor module 102 also includes a mount 244 as shown in FIG. 4. The mount 244 facilitates attachment to the mounting bracket 110. Illustratively, the mount 244 includes a mounting tab 246 and several alignment tabs 248. Of course, the mount 244 may have other or additional structures and/or features in other embodiments to facilitate the securement of the reference sensor module 102 to the mounting bracket 110. Regardless of the specific configuration, the reference sensor module 102 may be attached to a sensor mount base 112 of the mounting bracket 110 using the mount 244. For example, in the illustrative embodiment, the mounting tab 246 is received in a corresponding aperture of the sensor mount base 112 and the alignment tabs 248 clip to the side of the sensor mount base 112 to secure the reference sensor module 102 to the mounting bracket 110. As shown in FIG. 1, the mounting bracket 110 also includes an elongated rod 114 extending from the sensor mount base 112 to a bone mount base 116. The bone mount base 116 is configured to facilitate attachment of the mounting bracket 110 to the bony anatomy of the patient and may include one or more mounting aperture 118 configured to receive corresponding securing devices 120, such as bone screws or the like, to secure the mounting bracket 110 to the patient's bony anatomy.

The inserter sensor module 104 is similar to the reference sensor module 102. The housing 204 of the inserter sensor module 104 includes a top surface 250, a bottom surface 252, a front panel 254, side surfaces 256, 258, and a rear surface 260. The inserter sensor module 104 also includes a power button 270 and an alignment indicator 272 defined on the front panel 254. Similar to the power button 230 of the reference sensor module 102, the power button 270 is selectable to turn on the inserter sensor module 104 but not to subsequently turn off the inserter sensor module 104. That is, as discussed above with regard to the reference sensor module 102, re-selection of the power button 270 does not turn off the inserter sensor module 104 in some embodiments. Rather, the inserter sensor module 104 will remain on until the power source (e.g., internal batteries) of the inserter sensor module 104 is depleted as discussed in more detail below. Similar to the reference sensor module 102, the power button 270 of the inserter sensor module 104 may be backlit when the inserter sensor module 104 is powered on to provide a visual indication that the inserter sensor module 104 is on.

As discussed in more detail below, the alignment indicator 272 provides a visual feedback to the orthopedic surgeon whether the current alignment of the acetabular prosthetic component 160 is within a reference threshold of a target alignment. In the illustrative embodiment, the alignment indicator 272 includes a first threshold alignment indicator 274 and a second threshold alignment indicator 276. The first threshold alignment indicator 274 is embodied as a circular visual indicator, such as a circular light, circular array of light emitting diode, circular light filter, or the like. The first threshold alignment indicator 274 bounds the second threshold alignment indicator 276, which is embodied as a single visual indicator, such as a single light, light emitting diode, or the like. In use, the first threshold alignment indicator 274 is illuminated in response to the alignment of the acetabular prosthetic component 160 being within a first threshold of the reference alignment and the second threshold alignment indicator 276 is illuminated in response to the alignment of the acetabular prosthetic component 160 being within a second threshold of the reference alignment that is less than first threshold. That is, when the second threshold alignment indicator 276 is illuminated, the alignment of the acetabular prosthetic component 160 is closer to the reference alignment than when only the first threshold alignment indicator 274. Of course, in other embodiments, the alignment indicator 272 may include other or additional indicators.

As shown in FIG. 3, the housing 204 of the inserter sensor module 104 includes a keyed structure 280 defined on the top surface 250. As discussed above, the keyed structure 280 is keyed to the corresponding keyed structure 240 of the reference sensor module 102. In the illustrative embodiment, the keyed structure 280 is embodied as a recess 282 defined in the top surface 250 of the housing 204. Illustratively, the recess 282 has a shape corresponding to the shape of the raised platform 242 of the reference sensor module 102 such that the raised platform 242 may be received in the recess 282 when the sensor modules 102, 104 are coupled to together as discussed below. In the illustrative embodiment, the recess 282 has a substantially "Y"-shaped top profile and is arranged such that the width of the recess 282 is greater toward the front panel 254 and more narrow toward the rear surface 260. Of course, in other embodiments, other configurations of the keyed structure 280 that enable coupling of the sensor modules 102, 104 in a single orientation in which the keyed structures 240, 280 are mated may be used. For example, in some embodiments, the keyed structure 240 may be embodied as, or otherwise include, a raised platform, additional recesses, and/or other structures.

Similar to the reference sensor module 102, the inserter sensor module 104 also includes a mount 290 as shown in FIG. 4. The mount 290 facilitates attachment of the inserter sensor module to the acetabular prosthetic component inserter 130. The mount 290 is similar to the mount 244 of the reference sensor module 102 and includes a mounting tab 292 and several alignment tabs 294. Of course, the mount 290 may have other or additional structures and/or features in other embodiments to facilitate the securement of the inserter sensor module 104 to the acetabular prosthetic component inserter 130. In the illustrative embodiment, the sensor module 104 is attachable to the acetabular prosthetic component inserter 130 via use of a coupler 134. Similar to the mounting bracket 110, the coupler 134 includes a sensor mount base 136, which receives the mount 290 of the inserter sensor module 104. The coupler 134 is securable to a handle 138 of the acetabular prosthetic component inserter 130. An inserter rod 140 extends from the handle 138 and includes the distal end 132 to which the acetabular prosthetic component 160 is attached during insertion. Of course, acetabular prosthetic component inserters having different configurations may be used in other embodiments. Additionally, different mechanisms and structures may be used to attached the inserter sensor module 104 to the acetabular prosthetic component inserter 130 in other embodiments.

Figure 5:
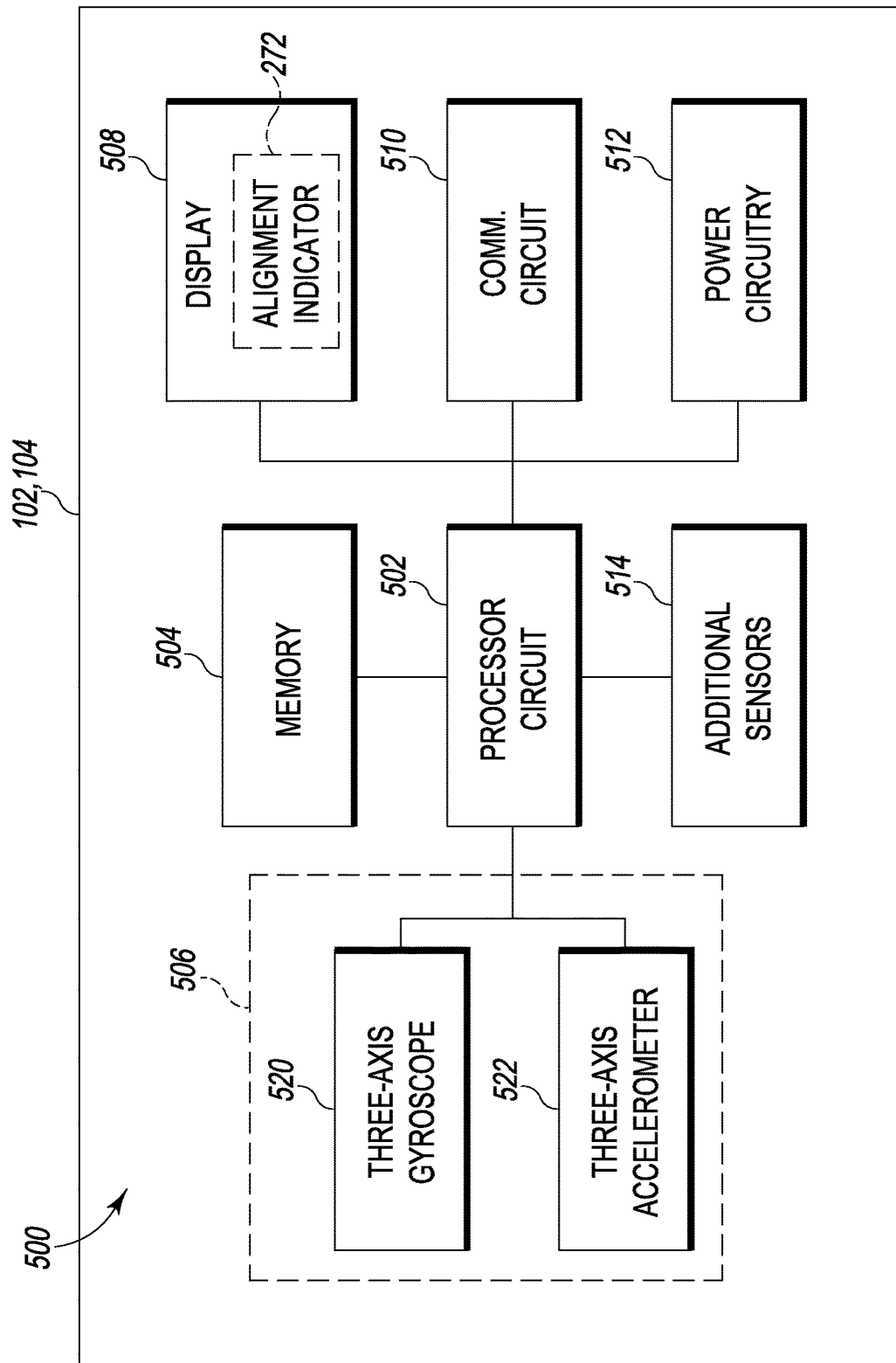
FIG. 5 is a simplified block diagram of a circuit of the reference sensor module and the inserter sensor module of FIG. 2.

Referring now to FIG. 5, each of the sensor modules 102, 104 includes a sensor circuit 500. The illustrative sensor circuit 500 includes a processor circuit 502, a memory 504, an orientation sensor 506, a display 508, a communication circuit 510, and power circuitry 512. Of course, each sensor module 102, 104 may include additional or other components typically found in sensing components, which have not been illustrated in FIG. 5 for clarity of the description.

The processor circuit 502 may be embodied as one or more processors and related components and/or circuitry. Such processors may be embodied as any type of processors capable of performing the functions described herein. For example, the processor(s) of the processor circuit 502 may be embodied as a single or multi-core processor(s) having one or more processor cores, a digital signal processor, a microcontroller, or other processor or processing/controlling circuit. Similarly, the memory 504 may be embodied as any type of volatile or non-volatile memory or data storage capable of performing the functions described herein. In operation, the memory 504 may store various data and/or software/firmware used during operation of the sensor modules 102, 104 including, for example, the temporary storage of orientation data generated by the orientation sensor 506. The memory 504, and other components of the sensor circuit 500, may be coupled to the processor circuit 502 and/or other components via various interconnects such as an I/O subsystem, control hubs/busses, firmware devices, communication links, and/or other components and subsystems to facilitate the input/output operations.

The orientation sensor 506 is configured to generate sensor data indicative of the orientation in three dimensions of the sensor module 102, 104. In the illustrative embodiment, the orientation sensor 506 is embodied as, or otherwise includes, a three-axis gyroscope 520 and a three-axis accelerometer 522. The three-axis gyroscope 520 may be embodied as any type of gyroscope sensor capable of measuring the rotation of the corresponding sensor module 102, 104 about the three coordinate axes. For example, the three-axis gyroscope 520 may be embodied as a single three-axis gyroscope or a collection of single axis gyroscopes. The three-axis accelerometer 522 may be embodied as any type of accelerometer capable of measuring acceleration of the sensor module 102, 104 along the three coordinate axes. Similar to the three-axis gyroscope 520, the three-axis accelerometer 522 may be embodied as a single three-axis accelerometer or as a collection of single axis accelerometers. The three-axis accelerometer 522 generates acceleration data used to correct biases in the output of the three-axis gyroscope 520 due to such acceleration. In the illustrative embodiment, the orientation sensor data generated by the orientation sensor 506 is represented as quaternion measurements. However, in other embodiments, the orientation sensor 506 may generate sensor data in other formats.

The display 508 is embodied as one or more illumination devices such as, for example, light emitting diodes, filament lights, and/or the other devices capable of illumination. The display 508 is positioned behind the power buttons 230, 270 of the sensor module 102, 104 to illuminate the power buttons 230, 270 when the sensor module 102, 104 is turned on. With regard to the inserter sensor module 104, the display 508 also includes the alignment indicator 272 as discussed above.

The communication circuit 510 may be embodied as one or more devices and/or circuitry for enabling communications between the sensor modules 102, 104 and the display module 106. The communication circuit 510 may be configured to use any suitable wireless communication protocol to communicate with the display module 106 including, for example, a short-range wireless communication protocol such as Bluetooth® or other wireless communication protocol.

The power circuitry 512 controls the activation of the sensor module 102, 104. In particular, as discussed above, the power circuitry 512 supplies power to other components of the sensor module 102, 104 in response to selection of the power button 230, 270. However, after the power button 230, 270 has been selected to turn on the sensor module 102, 104, the power circuitry 512 continues to supply such power to the components regardless of additional selections of the power button 230, 270. That is, the power circuitry 512 ensures that power is continuously supplied to the components of the sensor module 102, 104 until a power source (not shown) of the power circuitry 512 is depleted. In this way, the power circuitry 512 ensures that the sensor modules 102, 104 are single-use devices that cannot be reused in multiple surgeries.

In some embodiments, the sensor circuit 500 may also include additional sensors 514. The additional sensors 514 may include any number and type of sensors capable of improving the accuracy of the orientation sensor data generated by the orientation sensor 506. For example, the additional sensors 514 may include a temperature sensor in some embodiments. The sensor output of such a temperature sensor is used to further correct any biases of the sensor data generated by the orientation sensor 506 due to temperature. Of course, the sensor circuit 500 may include additional or other sensors in other embodiments to further increase the accuracy of the generated orientation sensor data.

Figure 6:
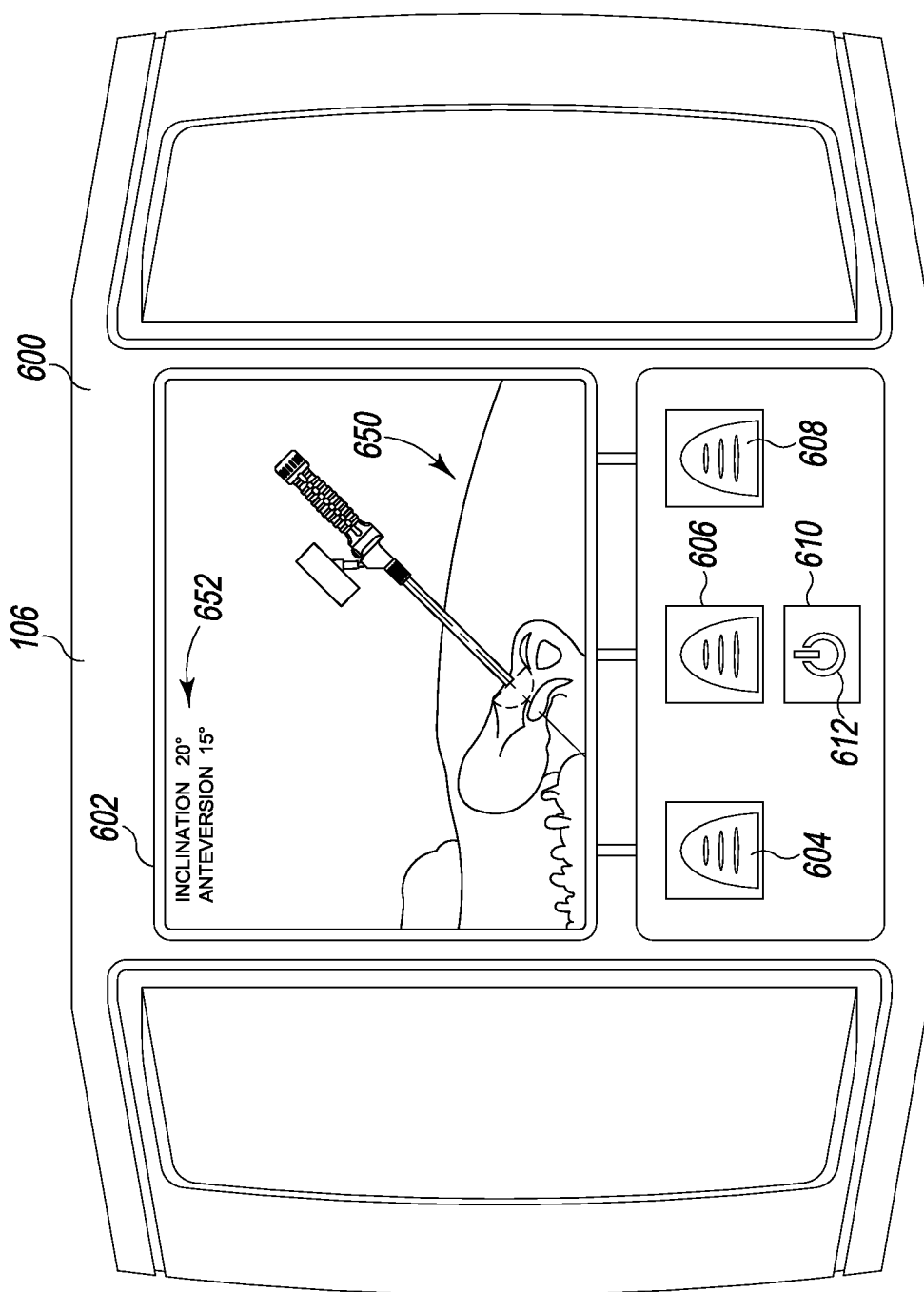
FIG. 6 is a simplified top plan view of a display module of the system of FIG. 1.

Referring now to FIG. 6, the display module 106 includes a housing 600 sized to be held in the hands of an orthopaedic surgeon and used during the performance of an orthopaedic surgical procedure. In this way, the display module 106 is configured to be mobile. The display module 106 also includes a display 602 on which visual indications of the orientation of the acetabular prosthetic component 160 relative to the patient's bony anatomy are displayed to the surgeon. For example, a visual graphic 650 showing a virtual inserter in a position relative to a virtual patient's bony anatomy that is indicative of the current positioning of the acetabular prosthetic component 160 relative to the actual patient's bony anatomy may be displayed on the display 602. Additionally or alternatively, the display 602 may include orientation data 652 identifying the determined degree or amount of inclination and/or anteversion of the acetabular prosthetic component 160 relative to the patient's bony anatomy as discussed in more detail below.

The display module 106 illustratively includes a plurality of user input buttons 604, 606, 608 positioned below the display 602. The user input buttons 604, 606, 608 may be "soft" buttons in that their functionality may change depending on the particular user interface displayed on the display 602. Additionally, the display module 106 includes a power button 610. The power button 610 may include a power indicator 612 to provide a visual indication as to when the display module 106 is turned on. In the illustrative embodiment, the power button 610 is positioned below the row of input buttons 604, 606, 608, but the buttons 604, 606, 608 may be positioned in other configurations and/or orientations in other embodiments.

Figure 7:
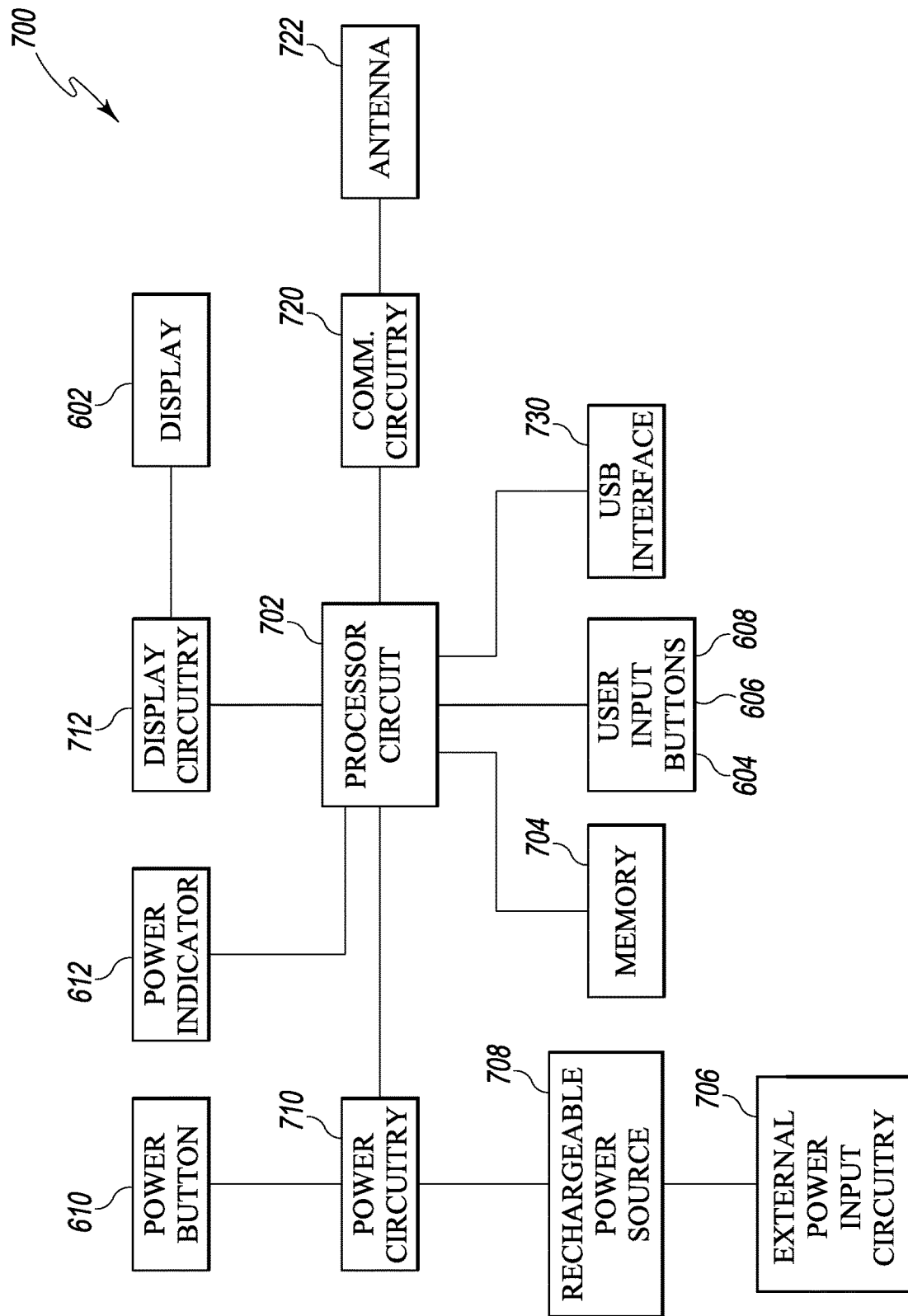
FIG. 7 is a simplified block diagram of a circuit of the display module of FIG. 6.

As illustrated in FIG. 7, the display module 106 includes a control circuit 700 positioned in the housing 600. The control circuit 700 includes a processor circuit 702 and a memory device 704. The processor circuit 702 may include, or be embodied as, any type of processor and related circuitry configurable to perform the functions described herein. For example, the processor(s) of the processor circuit 702 may be embodied as a single or multi-core processor(s) having one or more processor cores, a digital signal processor, a microcontroller, or other processor or processing/controlling circuit. Similarly, the memory device 704 may be embodied as any type of volatile or non-volatile memory or data storage capable of performing the functions described herein. In operation, the memory 704 may store various data and/or software/firmware used during operation of the display module 106.

The control circuit 700 also includes an external power input circuitry 706, a rechargeable power source 708 such as a rechargeable battery or the like, and power circuitry 710. The external power input circuitry 706 is configured to receive a plug of a charger such as a "wall charger" and is communicatively coupled to the rechargeable power source 708, which is communicatively coupled to the power circuitry 710. The power circuitry 710 is communicatively coupled to the processor circuit 702 and the power button 610. The power circuitry 710 may include power control, distribution, and filtering circuitry and is configured to provide or distribute power the rechargeable power source 708 to the processor circuit 702 and other devices or components of the control circuit 700.

The control circuit 700 also includes display circuitry 712 for driving and/or controlling the display 602. The display circuitry 712 is communicatively coupled to the processor circuit 702 and the display 602 to control functions thereof.

As discussed above, the display module 106 is configured to receive sensor data from each of the sensor modules 102, 104. As such, the control circuit 700 includes communication circuitry 720 and an antenna 722. The communication circuitry 720 is communicatively coupled to the processor circuit 702 and to the antenna 722. The communication circuitry 720 may be configured to use any type of wireless communication protocol, standard, or technologies to communicate with the sensor modules 102, 104 including, but not limited to, a short range wireless protocol such as a Bluetooth® protocol. As discussed in more detail below, in addition to receiving the orientation sensor data from each of the sensor modules 102, 104, the display module 106 may also be configured to communicate with the inserter sensor module 104 using the communication circuitry 720 to activate the alignment indicator 272 in response to determining that the current orientation of the acetabular prosthetic component 160 is within a reference threshold alignment relative to the patient's bony anatomy.

The control circuit 700 also includes a universal serial bus (USB) interface 730. The USB interface 730 is communicatively coupled to the processor circuit 702. The USB interface 730 may be used to download data, such as orientation data, from the display module 106 to another device such as a computer. Additionally, the USB interface 730 may be used to update the software or firmware of the control circuit 700.

Figure 8A:
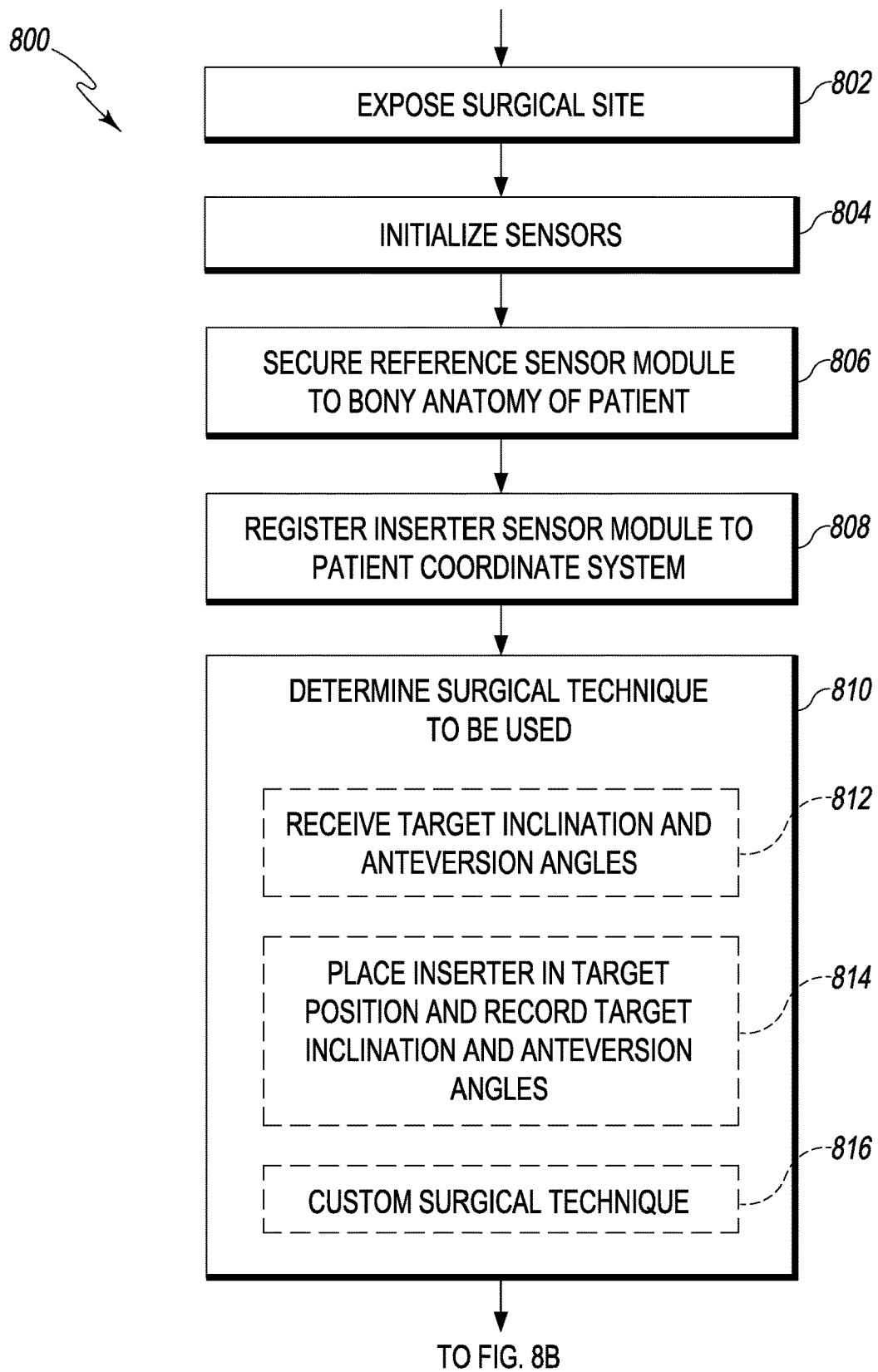
FIGS. 8A-8B are a simplified flow diagram of a method for aligning an acetabular prosthetic component in a patient's surgically prepared acetabulum.
Figure 8B:
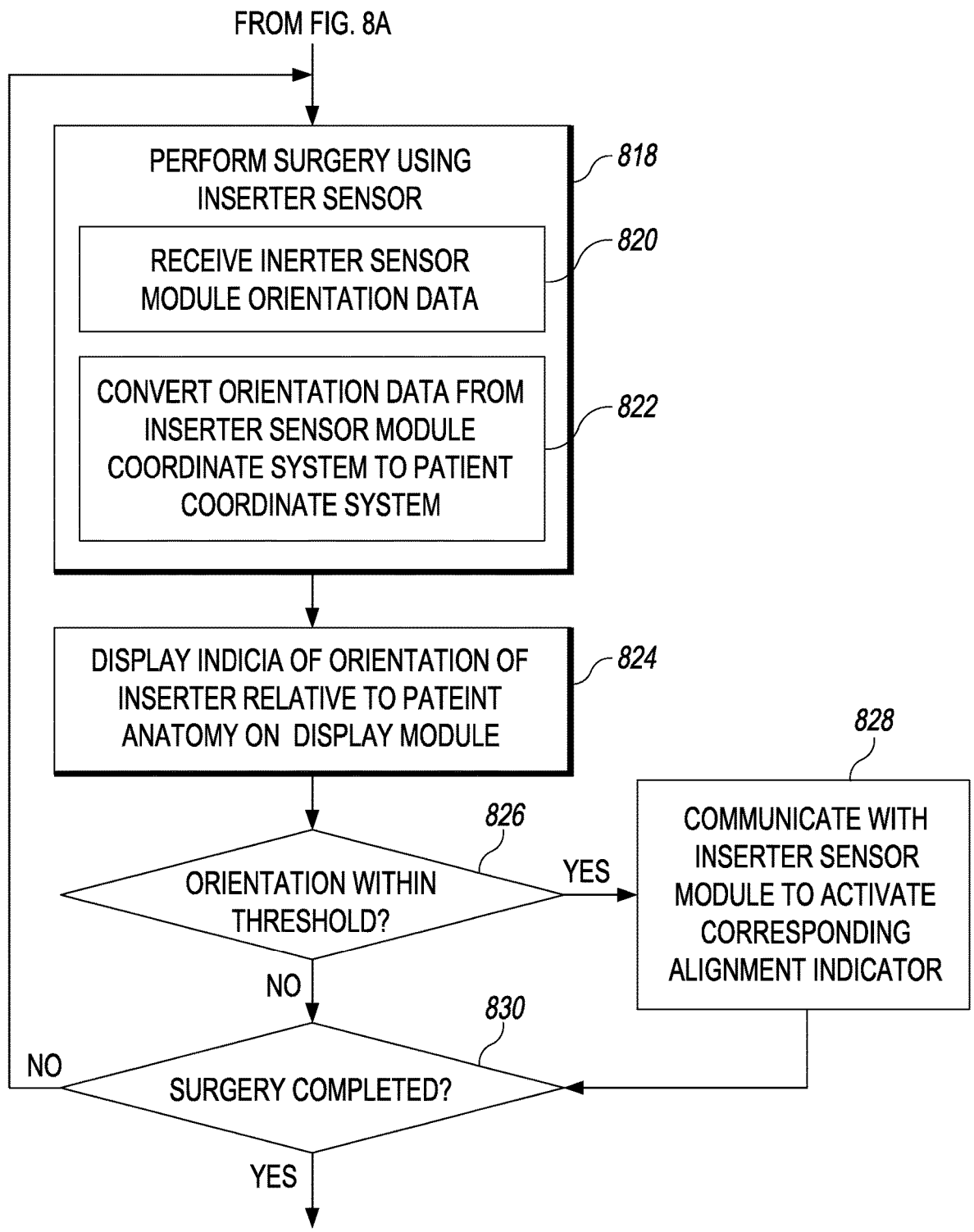
Figure 9:
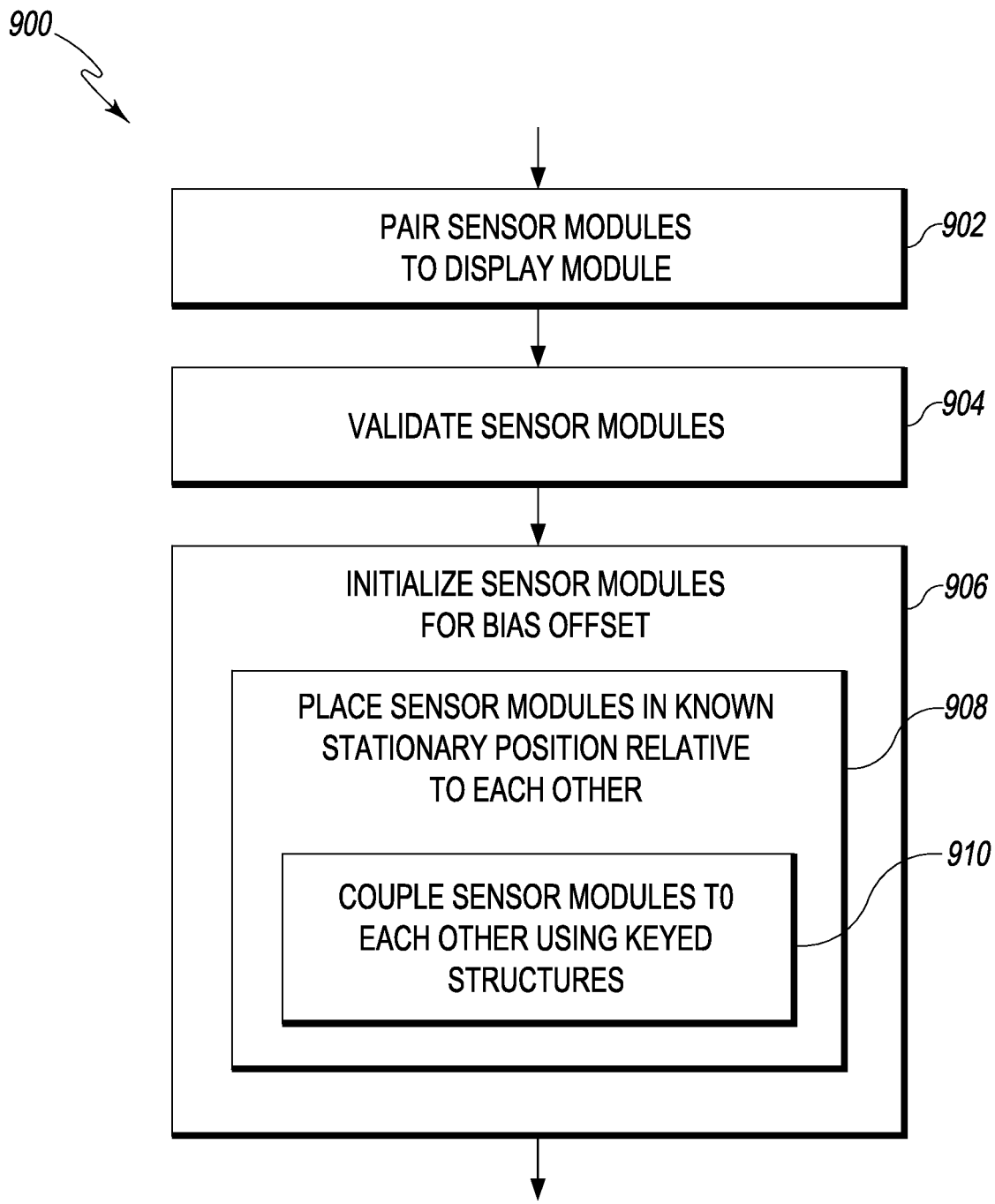
FIG. 9 is a simplified flow diagram of a method for initializing the reference sensor module and the inserter sensor module of FIG. 2.

Referring now to FIGS. 8A-8B, in use the system 100 may be used to perform a method 800 for aligning the acetabular prosthetic component 160 in a patient's surgically prepared acetabulum. The method begins with block 802 in which an orthopedic surgeon exposes the surgical site. Subsequently, in block 804 the reference sensor module 102 and the inserter sensor module 104 are initialized. For example, as shown in FIG. 9, a method 900 may be used to initialize the sensor modules 102, 104. The method 900 begins with block 902 in which each of the sensor modules 102, 104 is paired with the display module 106. Any suitable type of pairing procedure may be used to pair the sensor modules 102, 104 and the display module 106 depending on, for example, the type of communication protocol used to communicate between the sensor modules 102, 104 and the display module 106.

In block 904, the sensor modules 102, 104 are validated. For example, in the illustrative embodiment, each sensor module 102, 104 is configured to transmit identification data (e.g., a serial number, a MAC address, a global unique identifier, etc.) to the display module 106. In response, the display module 106 displays the received identification data so that the orthopaedic surgeon or other healthcare provider may validate that the current sensor modules are being used (e.g., by comparing the displayed identification data to identification data labeled on the housings 202, 204 of the sensor modules 102, 104, in associated packaging, etc.).

Figure 13:
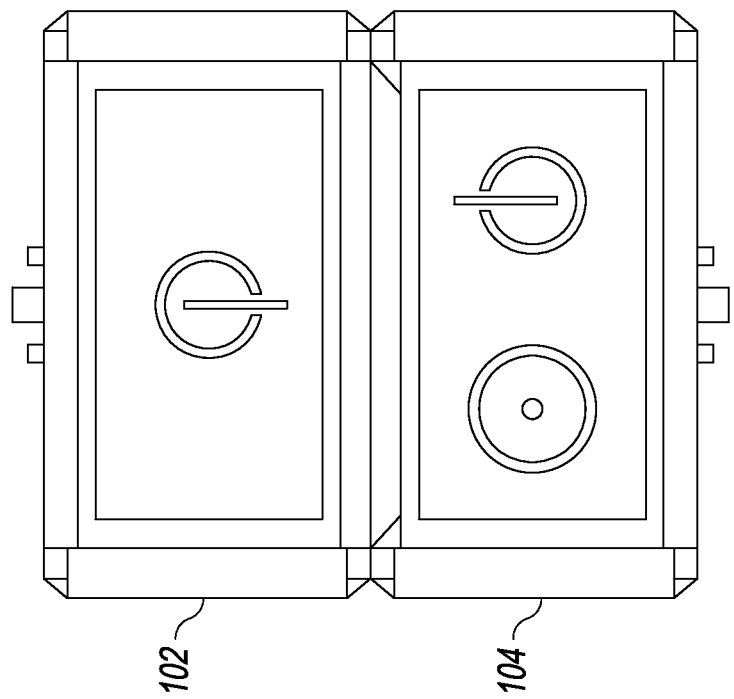
FIG. 13 is a simplified illustration of the reference sensor module and the inserter sensor module of the system coupled to each other using keyed features of the housings of the sensor modules.
Figure 12:
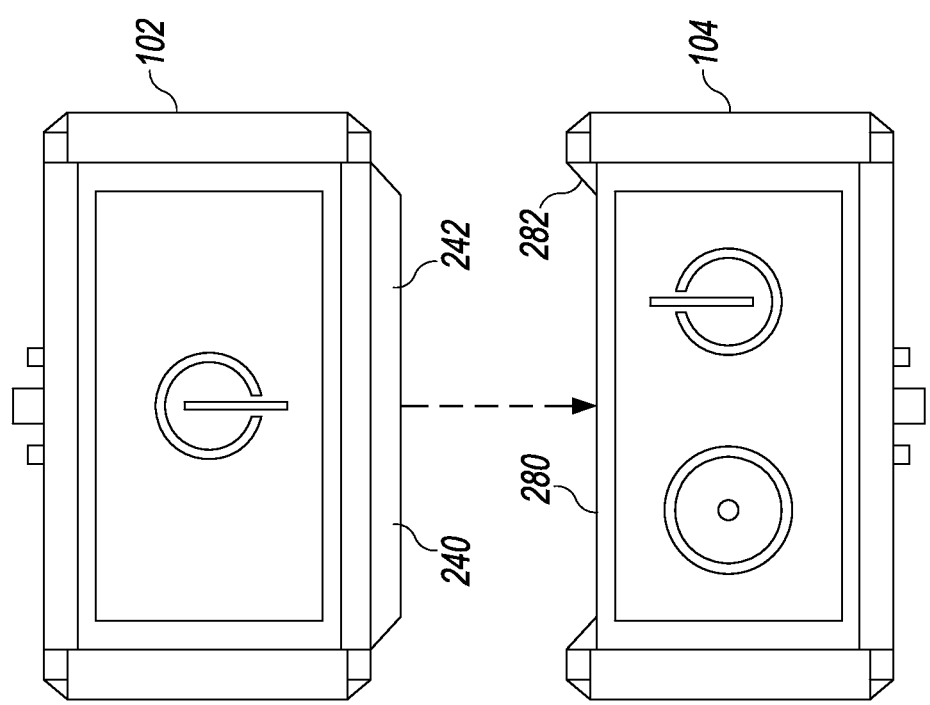
FIG. 12 is a simplified illustration of one initialization process of the reference sensor module and the inserter sensor module of the system of FIG. 1.

After the sensor modules 102, 104 have been validated in block 904, the sensor modules 102, 104 may be initialized to compensate for any bias offset of the orientation sensors 506 in block 906. For example, in some embodiments, each sensor module 102, 104 may be placed in a known stationary position relative to each other (e.g., placed stationary on a flat surface) in block 908. In the illustrative embodiment, the reference sensor module 102 and the inserter sensor module 104 are coupled together in a stationary position using the keyed structures 240, 280 to initialize the sensor modules 104, 106 in block 910. For example, as shown in FIGS. 12 and 13, the sensor modules 102, 104 may be coupled together by mating the keyed structure 240 of the reference sensor module 102 with the keyed structure 280 of the inserter sensor module 104. For example, in the illustrative embodiment, the raised platform 242 of the reference sensor module 102 is received in the corresponding recess 282 of the inserter sensor module 104. When so coupled, the top surface 210 of the reference sensor module 102 abuts the top surface 250 of the inserter sensor module 104 as shown in FIG. 13.

In some embodiments, the sensor modules 102, 104 may be coupled to each other in such mated configuration for a period of time or until the display module 106 indicates that the sensor modules 102, 104 have been properly initialized. In other embodiments, the sensor modules 102, 104 are not turned on initially until the sensor modules 102, 104 are coupled to each other. For example, block 906 may be executed prior to blocks 902, 904 of the method 900).

Figure 14:
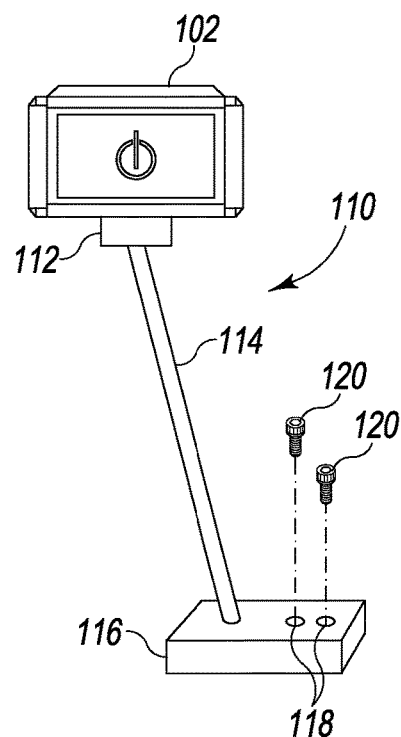
FIG. 14 is a simplified illustration of the reference sensor module of the system of FIG. 1 secured to a bone mounting bracket.
Figure 15:
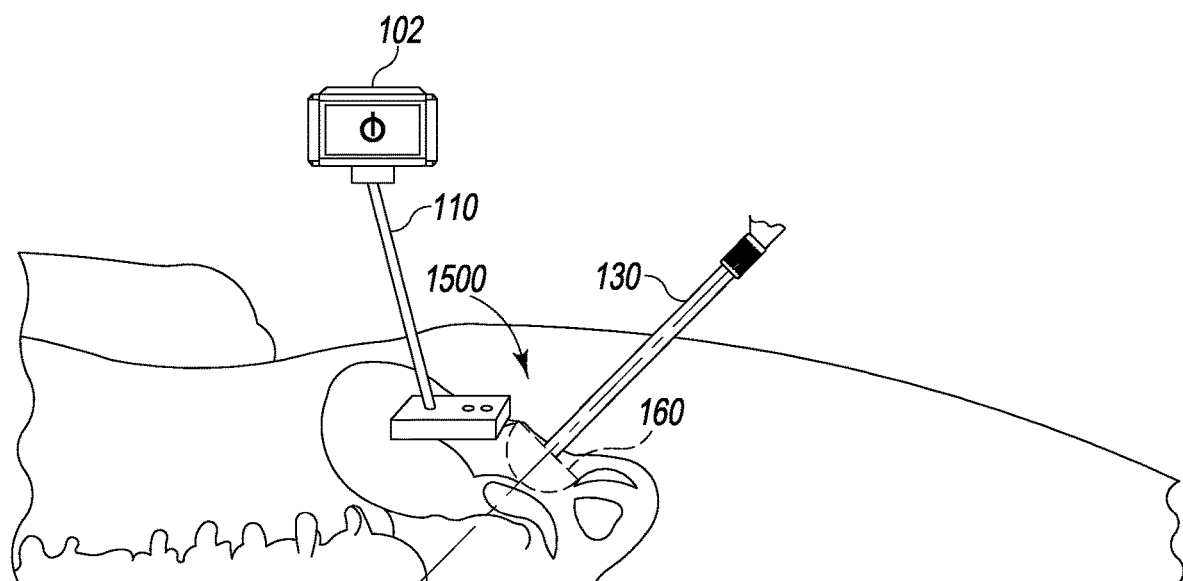
FIG. 15 is a simplified illustration of the reference sensor module of the system of FIG. 1 secured to a patient's bony anatomy using the mounting bracket of FIG. 14.

Referring back to the method 800 of FIGS. 8A-8B, after the sensor modules 102, 104 have been initialized in block 804, the reference sensor module 102 is secured to the patient's bony anatomy in block 806. To do so, as discussed above and shown in FIGS. 14 and 15, the reference sensor module 102 may be attached to the sensor mount base 112 of the mounting bracket 110 via the mount 244 of the housing 202 of the sensor module 102. The mounting bracket 110 may then be secured to the patient's bony anatomy via the bone mount base 116 using the securing devices 120. In the illustrative embodiment, as shown in FIG. 15, the reference sensor module 102 is secured to the patient's bony anatomy in the vicinity of the orthopedic surgical procedure. For example, the mounting bracket 110 may be secured near the patient's acetabulum 1500 as shown in FIG. 15.

Figure 17:
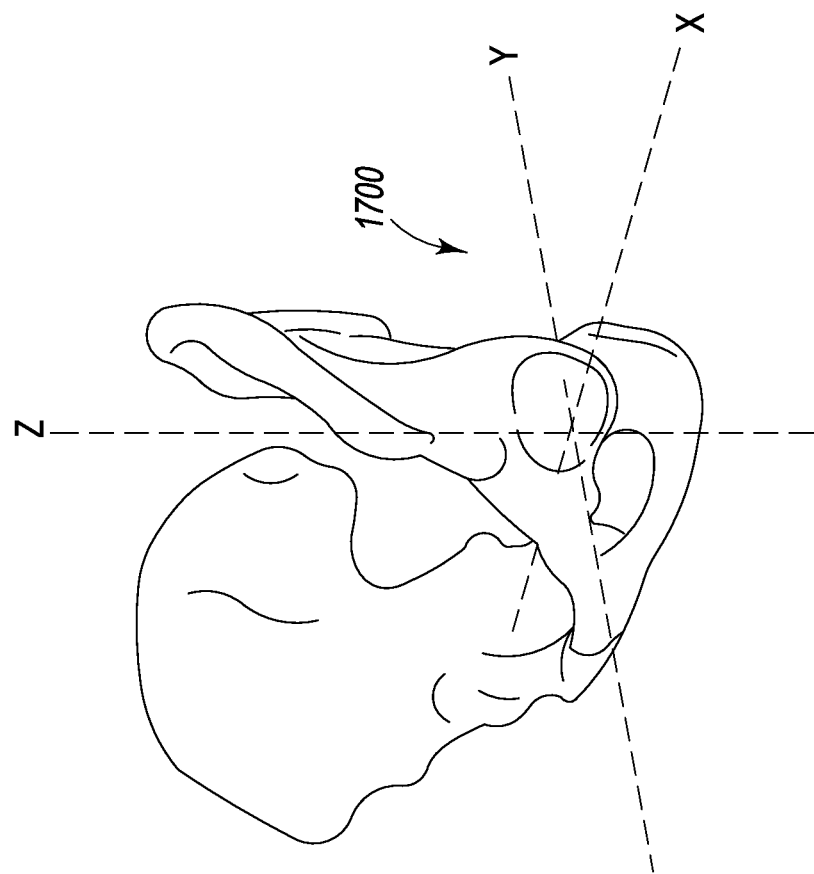
FIG. 17 is a simplified illustration of a patient coordinate system of the patient's bony anatomy.
Figure 16:
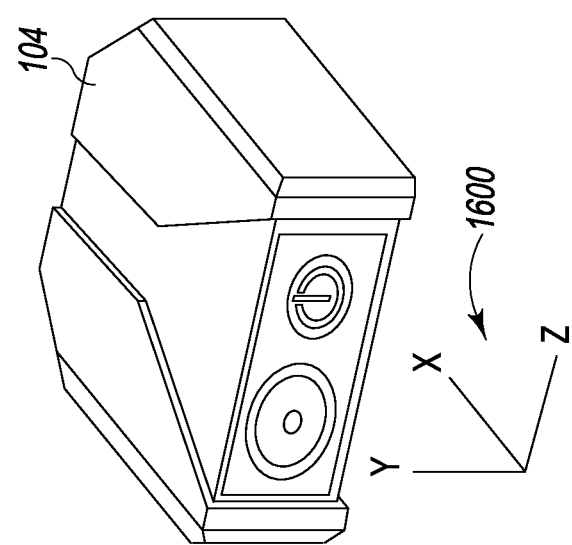
FIG. 16 is a simplified illustration of a coordinate system of the sensor modules of the system of FIG. 1.

Referring back to the method 800 of FIGS. 8A-8B, after the reference sensor module 102 has been secured to the patient's bony anatomy in block 806, the inserter sensor module 104 is registered to the coordinate system of the patient's bony anatomy. As shown in FIG. 16, the inserter sensor module 104 includes a sensor coordinate system 1600. The orientation sensor data generated by the inserter sensor module 104 is in reference to the sensor coordinate system 1600. However, as shown in FIG. 17, the patient's bony anatomy has a separate coordinate system 1700, which is not aligned with the sensor coordinate system 1600. As such, the inserter sensor module 104 is registered to the patient coordinate system 1700 so that the orientation sensor data generated by the inserter sensor module 104 can be converted to the patient coordinate system 1700 and the orientation of the acetabular prosthetic component 160, relative to the patient's bony anatomy, may be determined and displayed to the orthopaedic surgeon. The coordinate systems 1600, 1700 shown in FIGS. 16, 17 are illustrative coordinate systems used in the system 100. However, it should be appreciated that other coordinate system (e.g., coordinate systems having different axes) may be used in other embodiments.

Figure 10:
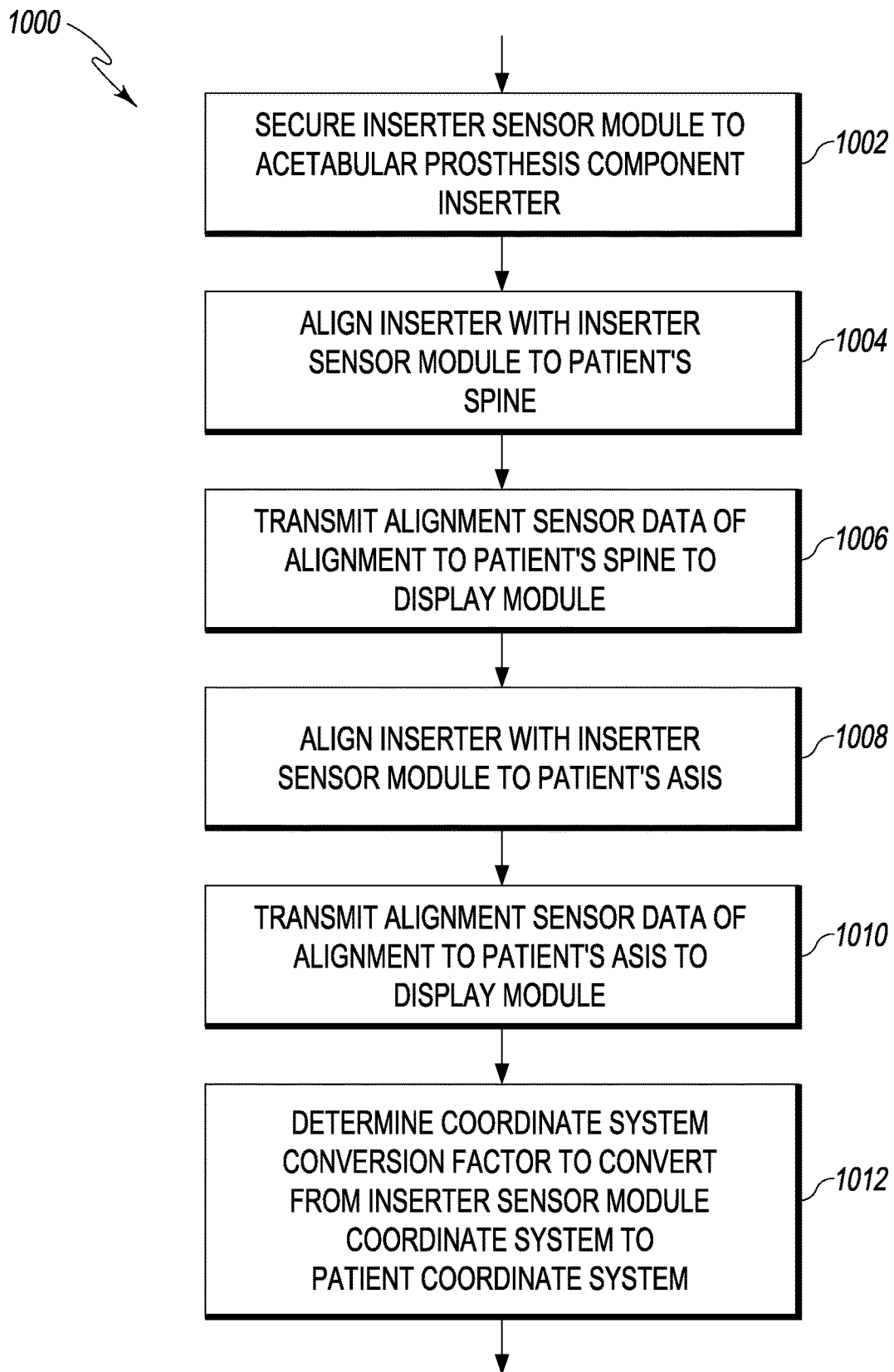
FIG. 10 is a simplified flow diagram of a method for registering the inserter sensor module of the system of FIG. 1 to a patient coordinate system of the patient's bony anatomy.

Referring to FIG. 10, a method 1000 for registering the inserter sensor module 104 with the patient coordinate system is shown. The method 1000 begins with block 1002 in which the inserter sensor module 104 is secured to the acetabular prosthetic component inserter 130. As discussed above, the inserter sensor module 104 may be secured to the acetabular prosthetic component inserter 130 using the coupler 134. For example, the mount 290 of the inserter sensor module 104 may be attached to the sensor mount base 136 of the coupler 134. The coupler 134 may subsequently be attached to the inserter handle 138. However, as discussed above, other mechanisms and structures may be used to attach the inserter sensor module 104 to the acetabular prosthetic component inserter 130 in other embodiments.

Figure 19:
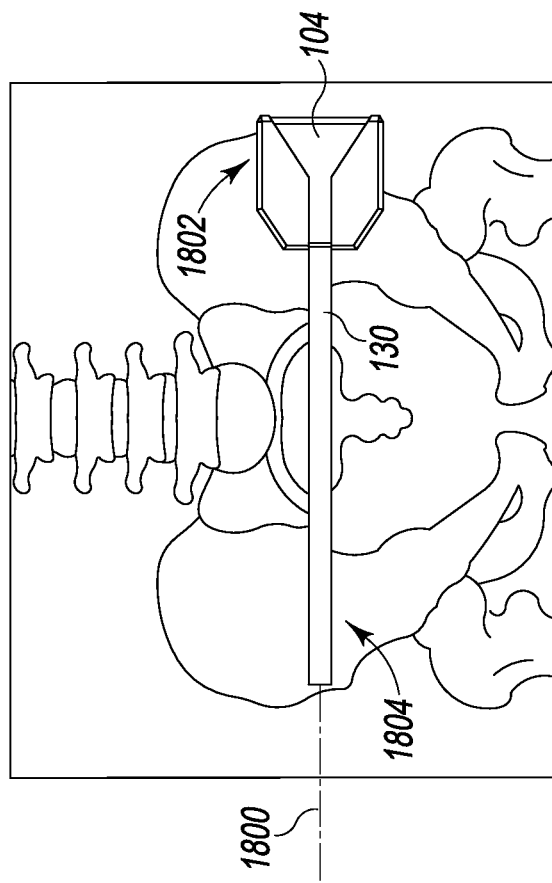
FIG. 19 is a simplified illustration of the inserter sensor module of the system of FIG. 1 aligned with an anatomical axis of the patient defined by the anterior superior iliac spine points of the patient's bony anatomy.
Figure 18:
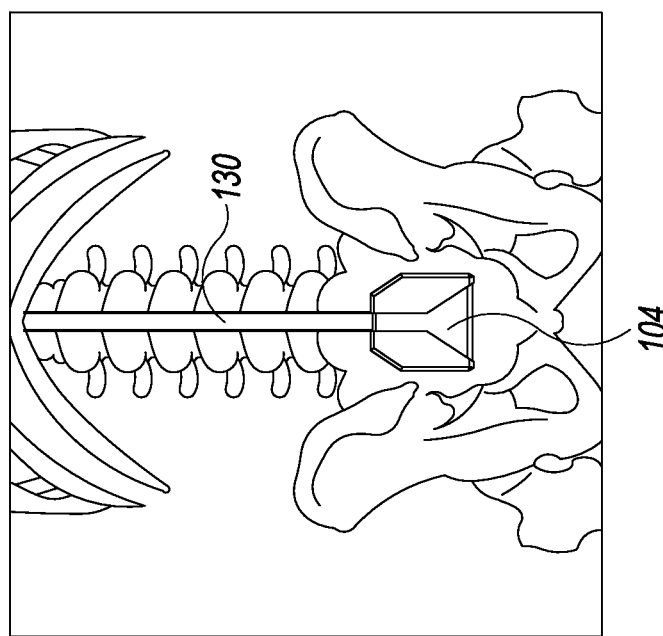
FIG. 18 is a simplified illustration of the inserter sensor module of the system of FIG. 1 aligned with the spine of the patient.

In block 1004, the acetabular prosthetic component inserter 130 with the attached inserter sensor module 104 is aligned with the patient's spine. To do so, as shown in FIG. 18, the acetabular prosthetic component inserter 130 may be aligned with the patient's spine by positioning the inserter 130 approximately in line with an axis defined by the patient's spine. Once so aligned, the sensor module 104 transmits alignment sensor data (i.e., the current orientation sensor data) to the display module 106 in block 1006. Subsequently, in block 1008, the acetabular prosthetic component inserter 130 with the attached inserter sensor module 104 is aligned with the patient's anterior superior iliac spine (ASIS) axis. To do so, as shown in FIG. 19, the acetabular prosthetic component inserter 130 may be aligned with an anatomical axis 1800 of the patient defined by the patient's anterior superior iliac spine landmarks 1802, 1804. Once so aligned, the sensor module 104 transmits alignment sensor data (i.e., the current orientation sensor data) to the display module 106 in block 1010.

Figure 26:
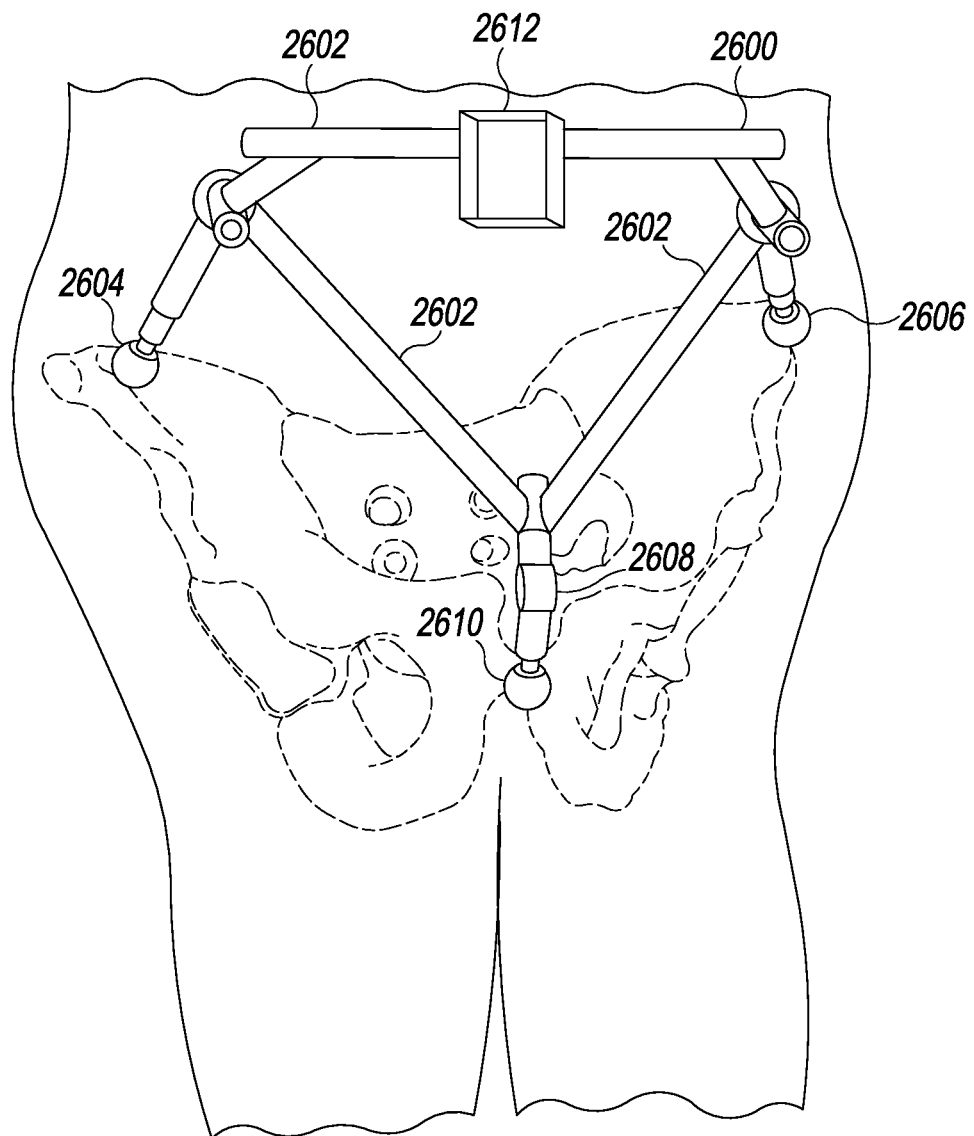
FIG. 26 is a simplified illustration of an embodiment of an alignment frame that may be used to register the inserter senor module of FIG. 1 with a patient coordinate system.

In other embodiments, the inserter sensor module 104 may be registered to the patient coordinate system using a 1-step registration process (rather than the dual alignment of blocks 1004 and 1008). To do so, an alignment frame 2600 may be used as shown in FIG. 26. The alignment frame 2600 includes a frame body 2602 having a pair of ASIS contact feet 2604, 2606 configured to contact the ASIS points of the patient. In some embodiments the contact feet 2604, 2606 are movable with respect to the frame body 2602 to allow the alignment frame 2600 to be used with patients of varying sizes. The alignment frame 2600 also includes a pubic symphysis arm 2608 extending distally from the frame body 2602 and movable with respect to the frame body 2602. The pubic symphysis arm 2608 includes a contact foot 2610 configured to contact the patient's pubic symphysis. Similar to the contact feet 2604, 2606, the contact foot 2610 may be movable, in addition to the pubic symphysis arm 2608, to accommodate patients of various sizes and improve the ease of coupling the alignment frame 2600 to the patient. The alignment frame 2600 also includes a cradle 2612, which is configured to receive the inserter sensor module 104. As such, to register the inserter sensor module 104 to the patient coordinate system, the alignment frame 2600 may be coupled, or otherwise placed on top of, the patient such that the contact feet 2604, 2606 rest on the patient's ASIS points and the contact foot 2610 rests on or contacts the patient's pubic symphysis. Once so positioned, the inserter sensor module 104 may be placed in the cradle 2612 and registered to the patient coordinate system. As with blocks 1006, 1010, the inserter sensor module 104 transmits alignment sensor data (i.e., the current orientation sensor data) to the display module 106 while secured to the alignment frame 2600 to register the inserter sensor module 104 to the patient coordinate system.

Figure 11A:
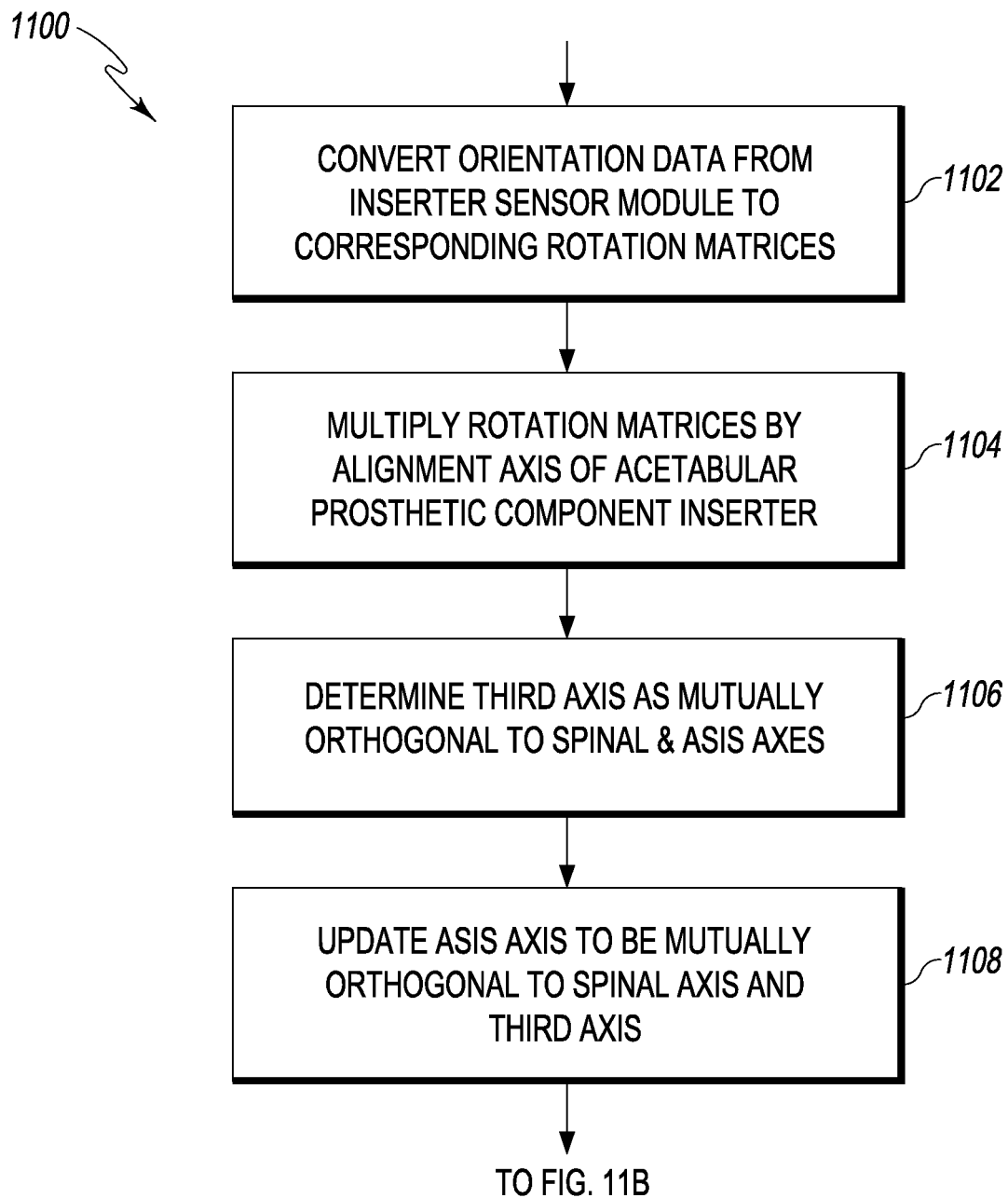
FIGS. 11A-11B are a simplified flow diagram of a method for determining a coordinate system conversion factor to convert from a coordinate system of the inserter sensor module to the patient coordinate system of the patient's bony anatomy.
Figure 11B:
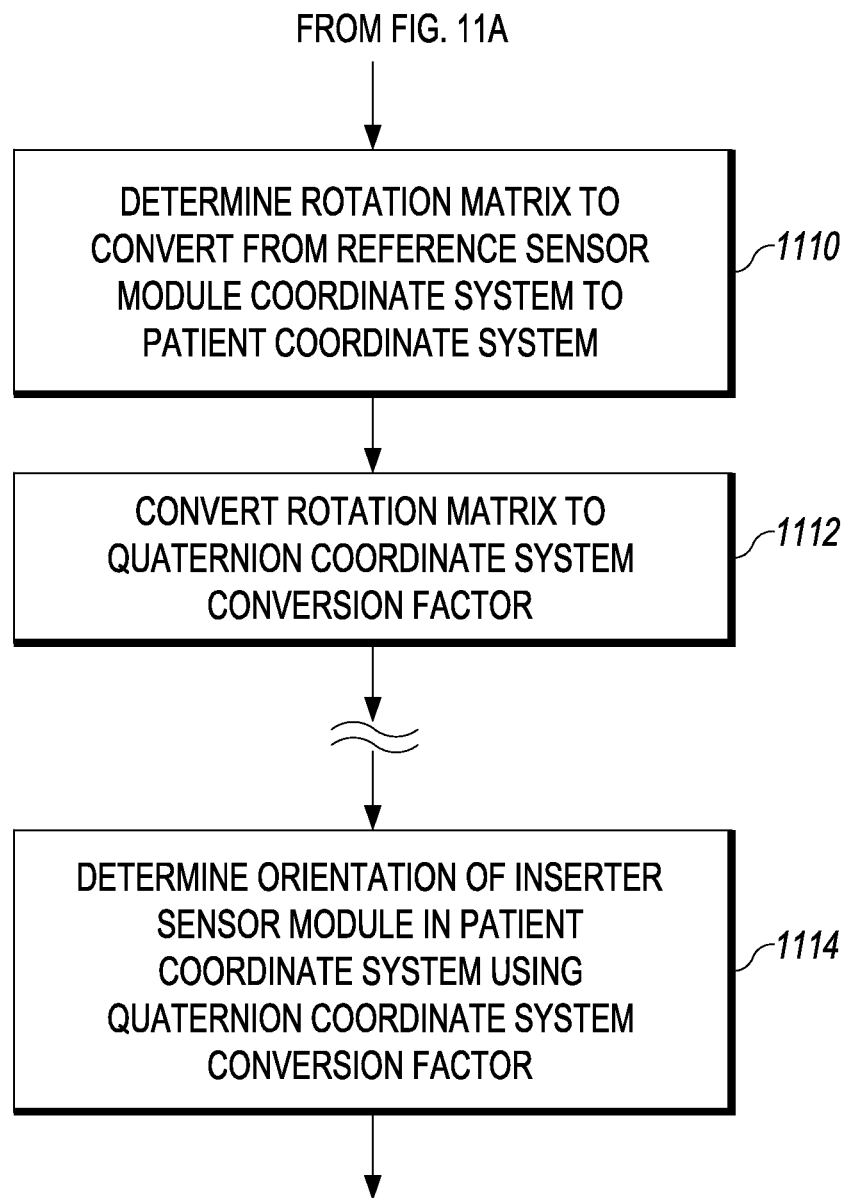

Referring back to FIG. 10, after receiving the alignment sensor data from the inserter sensor module 104 in blocks 1006, 1010, the display module 106 determines a coordinate system conversion factor in block 1012. The coordinate system conversion factor is usable to convert the orientation sensor data received from the inserter sensor module 104 from the sensor coordinate system 1600 to the patient coordinate system 1700. The coordinate system conversion factor may be embodied as any data usable to perform such function. For example, in the illustrative embodiment in which the sensor modules 102, 104 generate sensor data in a quaternion format, the display module 106 may execute a method 1100 such as the one shown in FIGS. 11A-11B for determining a coordinate system conversion factor to convert the orientation sensor data from the sensor coordinate system 1600 to the patient coordinate system 1700. The method 1100 begins with block 1102 in which the alignment orientation data received in blocks 1006, 1100, which is received in quaternion format, is converted to a rotation matrix. The quaternion format of the orientation data is generally of the form: $Q=qw+i*qx+j*qy+k*qz$, wherein Q defines a rotation about a vector $[Qx, Qy, Qz]$ by an angle of $2*\cos^{-1}(Qw)$.

To convert the quaternion format to a rotation matrix, the display module 106 utilizes a rotation matrix equation 2000 as shown in FIG. 20. Subsequently, in block 1104, the rotation matrix generated in block 1102 is multiplied by the alignment axis of the acetabular prosthetic component inserter 130 (i.e., the spinal and ASIS axes of the patient). To do so, the display module 106 may utilize a spinal axis vector equation 2100 and an ASIS vector equation 2102 as shown in FIG. 21. The third axis is determined in block 1106 as mutually orthogonal to the spinal and ASIS axes. The display module 106 may utilize a vector equation 2104, shown in FIG. 21, to determine the mutually orthogonal third axis. Subsequently, in block 1108, the display module 106 updates the ASIS axis vector to be mutually orthogonal to the spinal axis and the third axis calculated in block 1106 using a vector equation 2200 shown in FIG. 22. In some embodiments, if the updated ASIS axis vector is different from the previous ASIS axis vector by a reference threshold amount, the display module 106 may offer the orthopaedic surgeon the option to re-register the inserter sensor module 104 to the patient coordinate system 1700.

In block 1110, a rotation matrix to convert from the sensor coordinate system of the reference sensor module 102 to the patient coordinate system 1700 is determined. To do so, the display module 106 utilizes a rotation equation 2300 as shown in FIG. 23. In block 1112, the display module then converts the rotation matrix determined in block 1110 to a quaternion coordinate system conversion factor using as quaternion equation 2400 as shown in FIG. 24. Subsequently, during the performance of the orthopaedic surgical procedure and as discussed in more detail below, the orientation data received from the inserter sensor module 104 (Q2) may be converted, in block 1114, from the sensor coordinate system 1600 to the patient coordinate system 1700 using the quaternion conversion equation 2500 shown in FIG. 25. Of course, it should be appreciated that other coordinate system conversion factors may be calculated, or otherwise determined, in other embodiments based on the type of orientation sensors 506 and/or the orientation data generated by such sensors 506.

Referring back to method 800 of FIGS. 8A-8B, after the inserter sensor module 104 has been registered with the patient coordinate system in block 808, the orthopaedic surgeon may select the type of orthopaedic surgery to be performed in block 810. To do so, various surgery options may be displayed to the orthopedic surgeon on the display 602 of the display module 106. The orthopaedic surgeon may select the appropriate surgery type of the displayed options or otherwise provide input to the display module 106 to select or define the desired surgery type or features. For example, in block 812 the surgeon may select a targeted surgical approach in which the orthopaedic surgeon selects or supplies a targeted orientation of the acetabular prosthetic component 160 relative to the patient's bony anatomy. To do so, the orthopaedic surgeon may, for example, enter a desired inclination angle and/or a desired anteversion angle in block 812. Alternatively, in block 814, the orthopaedic surgeon may manually position the acetabular prosthetic component 160 into the patient's acetabulum in the desired final orientation using the acetabular prosthetic component inserter 130. Once so positioned, the display module 106 may capture the orientation data (e.g., the inclination and anteversion angles) of the acetabular prosthetic component 160 while it is placed in the desired position. Such orientation data may be subsequently used as the target orientation of the acetabular prosthetic component 160 during the orthopaedic surgery. In other embodiments, the orthopaedic surgeon may opt for a custom surgical technique in block 816 in which no target orientation is predetermined or otherwise supplied prior to the orthopaedic surgery. Rather, the surgeon may use the orientation data displayed by the display module 106 during the orthopaedic surgery as feedback in selecting the proper orientation (i.e., the proper inclination and anteversion angles).

After the surgical technique has been selected or determined in block 810, the method 800 advances to block 818 in which the orthopaedic surgeon performs the orthopaedic surgery using the system 100. During performance of the orthopaedic surgery, the display module 106 receives orientation sensor data from each of the reference sensor module 102 and the inserter sensor module 104 in block 820. In block 822, the display module 106 converts the orientation sensor data received from the inserter sensor module 104 from the sensor coordinate system 1600 to the patient coordinate system 1700 using the coordinate system conversion factor as discussed above in regard to method 1100. As such, the orientation of the acetabular prosthetic component 160 may be determined relative to the patient coordinate system 1700 based on the conversion of the orientation sensor data received from the inserter sensor module 104.

In block 824, the display module 106 displays indicia of the orientation of the acetabular prosthetic component 160 relative to the patient's bony anatomy on the display 602. As discussed above, the indicia may be embodied as a graphic 650 of a virtual inserter positioned relative to a virtual bony anatomy of the patient based on the determined orientation of the acetabular prosthetic component 160 and/or textual orientation data 652 that provides a numerical value of the orientation, such as the relative inclination and/or anteversion angles.

In block 826, the display module 106 determines whether the determined orientation of the acetabular prosthetic component 160 is within a reference threshold of a target orientation (e.g., the target orientation defined in block 810). If so, the method 800 advances to block 828 in which the display module 106 communicates with the inserter sensor module to activate the alignment indicator 272. As discussed above, in some embodiments, the alignment indicator may include a first threshold alignment indicator 274 and a second threshold alignment indicator 276. In such embodiments, the display module 106 determines which alignment indicator 272 should be illuminated based on the determined orientation and the target orientation of the acetabular prosthetic component 160 (i.e., which defined threshold amount is satisfied) and communicates with the inserter sensor module to activate the corresponding alignment indicator 272. The alignment thresholds corresponding to the first threshold alignment indicator 274 and a second threshold alignment indicator 276 may be defined as any type of threshold (e.g., a percentage or raw amount) and may be determined by the orthopaedic surgeon, the patient's anatomy, the orthopaedic surgical procedure, or otherwise based on other criteria. Regardless, after the alignment indicator has been activated in block 828, the method 800 advances to block 830.

If, in block 826, the display module 106 instead determines that the determined orientation of the acetabular prosthetic component 160 is outside of the reference threshold of the target orientation (e.g., the target orientation defined in block 810), or if the display module 106 determines the reference threshold of the target orientation has not been set, the method 800 advances to block 830. In block 830, it is determined whether the orthopaedic surgery has been completed. If not, the method 800 loops back to block 818 in which the orthopaedic surgeon continues the orthopaedic surgery.

The invention claimed is:

1. A system for aligning an acetabular prosthetic component in a patient's surgically prepared acetabulum, the system comprising:
    an inserter sensor module securable to an acetabular prosthetic component inserter, the inserter sensor module including (i) an orientation sensor configured to generate sensor data indicative of the orientation of the acetabular prosthetic component inserter in three-dimensions while the inserter sensor module is secured to the acetabular prosthetic component inserter and (ii) a communication circuit to transmit the sensor data; and
    an alignment frame configured to be placed on a body of the patient, the alignment frame having a frame body, a plurality of contact feet configured to be positioned on the body of the patient to confront corresponding reference points of the patient's bony anatomy, and a cradle configured to receive the inserter sensor module, wherein the inserter sensor module is further configured to transmit, via the communication circuit, alignment data produced by the orientation sensor and indicative of the current orientation of the inserter sensor module while the inserter sensor module is received in the cradle, wherein the alignment data is usable to register the inserter sensor module to a patient coordinate system of the patient's bony anatomy.

2. The system of claim 1, wherein the plurality of contact feet includes a pair of contact feet and each of the pair of contact feet is independently movable relative to the frame body.

3. The system of claim 2, wherein each foot of the pair of contact feet is an anterior superior iliac spine (ASIS) contact foot and is movable relative to the frame body to a position on the body of the patient that confronts a corresponding ASIS point of the patient's bony anatomy.

4. The system of claim 2, wherein the alignment frame further includes an arm extending distally from the frame body, wherein the arm includes a contact foot of the plurality of contact feet.

5. The system of claim 4, wherein the contact foot of the arm is movable relative to the frame body.

6. The system of claim 5, wherein the arm is a pubis symphysis arm and the contact foot of the arm is movable relative to the frame body to a position on the body of the patient that confronts the pubic symphysis of the patient.

7. The system of claim 1, further comprising a display module separate from the inserter sensor module, the display module including (i) a display, (ii) a communication circuit configured to receive the alignment data and the sensor data from the inserter sensor module, and (iii) a processing circuit to determine a coordinate system conversion factor to convert the sensor data received from the inserter sensor module from a coordinate system of the inserter sensor module to a patient coordinate system of the patient's bony anatomy and determine an orientation of the acetabular prosthetic component inserter relative to the patient's bony anatomy using the coordinate system conversion factor and the sensor data received from the inserter sensor module.

8. The system of claim 7, wherein the orientation sensor of the inserter sensor module comprises a second orientation sensor configured to generate second sensor data indicative of the orientation of the acetabular prosthetic component inserter in three-dimensions while the inserter sensor module is secured to the acetabular prosthetic component inserter and the communication circuit of the inserter sensor module comprises a second communication circuit to transmit the second sensor data, and further comprising:
    a reference sensor module securable to the patient's bony anatomy and including (i) a first orientation sensor configured to generate first sensor data indicative of the orientation of the patient's bony anatomy in three-dimensions and (ii) a first communication circuit to transmit the first sensor data,
    wherein the communication circuit of the display module is further to receive the first sensor data and the second sensor data, and
    wherein the processing circuit of the display module is further to determine the orientation of the acetabular prosthetic component coupled to the acetabular prosthetic component inserter relative to the patient's bony anatomy based on the first sensor data, the second sensor data, and the coordinate system conversion factor and display indicia of the determined orientation of the acetabular prosthetic component on the display.

9. The system of claim 8, wherein the inserter sensor module further includes an alignment indicator, and
    wherein the processing circuit of the display module is further to communicate with the inserter sensor module to activate the alignment indicator in response to the determined orientation of the acetabular prosthetic component being within threshold amount of a reference orientation.

10. The system of claim 8, wherein each of the reference sensor module and the inserter sensor module includes a power button selectable to turn on the corresponding sensor module, and wherein each of the reference sensor module and the inserter sensor module is incapable of being turned off by selection of the power button after the corresponding sensor module has been turned on.

11. The system of claim 8, wherein the processing circuit of the display module is configured to determine an inclination angle and an anteversion angle of the acetabular prosthetic component relative to the patient's bony anatomy and display the inclination angle and the anteversion angle on the display.

12. The system of claim 11, wherein the processing circuit of the display module is configured to display a graphical representation of the acetabular prosthetic component inserter on the display in a position based on the determined inclination angle and anteversion angle.

\* \* \* \* \*